US007547721B1

(12) United States Patent
Miwa et al.

(10) Patent No.: US 7,547,721 B1
(45) Date of Patent: *Jun. 16, 2009

(54) NEAR INFRARED FLUORESCENT CONTRAST AGENT AND FLUORESCENCE IMAGING

(75) Inventors: Naoto Miwa, Osaka (JP); Michihito Inagaki, Osaka (JP); Hiroaki Eguchi, Hyogo (JP); Masafumi Okumura, Shiga (JP); Yoshio Inagaki, Kanagawa (JP); Toru Harada, Kanagawa (JP)

(73) Assignees: Bayer Schering Pharma AG, Berlin (DE); Fuji Photo Film Co., Ltd., Kanagawa (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/149,917

(22) PCT Filed: Dec. 15, 1999

(86) PCT No.: PCT/EP99/09959

§ 371 (c)(1),
(2), (4) Date: Oct. 17, 2002

(87) PCT Pub. No.: WO01/43781

PCT Pub. Date: Jun. 21, 2001

Related U.S. Application Data

(63) Continuation-in-part of application No. 09/787,394, filed as application No. PCT/EP99/07088 on Sep. 16, 1999.

(30) Foreign Application Priority Data

Sep. 18, 1998 (JP) .................................. 10-283301

(51) Int. Cl.
A61K 31/404 (2006.01)
(52) U.S. Cl. ...................................... 514/414; 514/415
(58) Field of Classification Search .................. 424/9.6; 514/415, 412, 411, 339, 407, 414; 546/277.4; 548/364.7, 427, 455; 544/373
See application file for complete search history.

(56) References Cited

U.S. PATENT DOCUMENTS

| | | | |
|---|---|---|---|
| 4,839,265 A * | 6/1989 | Ohno et al. .................. 430/522 |
| 4,871,656 A * | 10/1989 | Parton et al. ................. 430/522 |
| 5,298,379 A | 3/1994 | Adin et al. |
| 5,440,042 A * | 8/1995 | Fabricius et al. ............. 544/315 |
| 5,672,332 A | 9/1997 | Fung et al. |
| 5,672,333 A | 9/1997 | Rajagopalan et al. |
| 5,709,845 A | 1/1998 | Rajagopalan et al. |
| 5,723,204 A | 3/1998 | Stefik |
| 5,747,233 A | 5/1998 | Lonsky et al. |
| 5,863,753 A | 1/1999 | Haugland et al. |
| 6,083,485 A | 7/2000 | Licha et al. |
| 6,083,486 A | 7/2000 | Weissleder et al. |
| 6,114,350 A | 9/2000 | Randall et al. |
| 6,159,657 A * | 12/2000 | Fleming et al. .......... 430/270.1 |
| 6,258,340 B1 | 7/2001 | Licha et al. |
| 6,319,488 B1 | 11/2001 | Licha et al. |
| 6,329,531 B1 | 12/2001 | Turner et al. |
| 6,441,191 B1 | 8/2002 | Lonsky et al. |
| 6,498,945 B1 | 12/2002 | Alfheim et al. |
| 6,663,847 B1 | 12/2003 | Achilefu et al. |
| 2003/0202941 A1 | 10/2003 | Achilefu et al. |
| 2004/0213740 A1 | 10/2004 | Achilefu et al. |

FOREIGN PATENT DOCUMENTS

| | | |
|---|---|---|
| EP | 0 577 189 A2 | 1/1994 |
| EP | 0 580 145 A | 1/1994 |
| EP | 0 591 820 A | 4/1994 |
| EP | 0 800 831 A1 | 10/1997 |
| JP | 06-145539 * | 5/1994 |
| WO | WO 91 18006 A1 | 11/1991 |
| WO | WO 96 17628 A | 6/1996 |
| WO | WO 97 13490 A | 4/1997 |
| WO | WO 97 13810 A | 4/1997 |
| WO | WO 97 40104 A | 10/1997 |
| WO | WO 99 22146 A | 5/1998 |
| WO | WO 98 47538 A | 10/1998 |
| WO | WO 00 16810 A1 | 3/2000 |

OTHER PUBLICATIONS

Licha et al., "Synthesis and characterization of cyanine dyes as contrast agents for near-infrared imaging," Proceedings of the SPIE, US, SPIE, Bellingham, VA, vol. 2927, Sep. 9, 1996, pp. 192-198, XP002079648.
Riefke et al., "In vivo characterization of cyanine dyes as contrast agents for near-infrared imaging"; Proceedings of the SPIE, US, SPIE, Bellinghan, VA; vol. 2927, pp. 199-208.
Licha et al., "Synthesis and characterization of cyanine dye—poly(ethylene glycol) conjugates as contrast agents for in vivo fluorescence image"; Proceedings of the SPIE, US, SPIE; Bellingham, VA; vol. 3196, pp. 98-102.
Office Action dated Aug. 5, 2004, and Reply to Office Action filed Feb. 7, 2005, of U.S. Appl. No. 09/787,394, filed May 16, 2001.
Final Office Action dated Apr. 13, 2007 in U.S. Appl. No. 09/787,394, filed May 16, 2001.
Non-Final Office Action dated Jun. 22, 2007 in U.S. Appl. No. 10/324,010, filed Dec. 20, 2002.
Office Action dated Jun. 22, 2007 in pending U.S. Appl. No. 10/324,010, filed Dec. 20, 2002.
Office Action Dated Mar. 17, 2008 in U.S. Appl. No. 10/324,010, filed Dec. 20, 2002.
Notice of Allowance dated Jan. 16, 2008 in U.S. Appl. No. 09/787,394, filed May 16, 2001.

* cited by examiner

*Primary Examiner*—Bernard Dentz
(74) *Attorney, Agent, or Firm*—Millen, White, Zelano & Branigan, P.C.

(57) ABSTRACT

The present invention relates to a compound defined by a formula herein, a composition and/or a method relating to one or more of the defined compounds.

4 Claims, 8 Drawing Sheets

NEAR INFRARED FLUORESCENT CONTRAST AGENT AND FLUORESCENCE IMAGING

This application is the national phase of PCT/EP99/09959 filed Dec. 15, 1999 and published in English, which is a continuation in part of PCT/EP99/07088 filed on Sep. 16, 1999 and published in English, whose national phase is U.S. Ser. No. 09/787,394, filed May 16, 2001.

TECHNICAL FIELD OF THE INVENTION

The present invention relates to a near infrared fluorescent contrast agent and fluorescence imaging using said contrast agent.

In treating diseases, it is vital to detect morphological and functional changes caused by the disease in the living body at an early stage of the disease. Especially when treating cancer, the site and size of tumor are significant determinant factors of the effective treatment design. Known methods for this purpose include biopsy by puncture and the like, and imaging diagnoses such as X-ray imaging, MRI, ultrasound imaging and the like. Biopsy is effective for definitive diagnosis, but at the same time it places great burden on test subjects and is not suitable for tracking time-course changes in lesions. X-ray imaging and MRI inevitably expose test subjects to radiation and magnetic waves. In addition, conventional imaging diagnoses as mentioned above require complicated operation and a long time for measurement and diagnosis. A large apparatus used for this purpose also makes it difficult to apply these methods during operation.

One of the image diagnoses is fluorescence imaging (Lipspn R. L. et al., *J. Natl. Cancer Inst.*, 26, 1-11 (1961)). This method uses, as a contrast agent, a substance that emits fluorescence upon exposure to an excitation light having a specific wavelength. Thus, a body is exposed to an excitation light from outside the body and the fluorescence emitted from the fluorescent contrast agent in the body is detected.

Such fluorescent contrast agent may be, for example, a porphyrin compound that accumulates in tumor and is used for photodynamic therapy (PDT), such as haematoporphyrin. Other examples include photophrin and benzoporphyrin (see Lipspn R. L. et al., supra, Meng T. S. et al., *SPIE*, 1641, 90-98 (1992), WO 84/04665 and the like). These compounds are originally used for PDT and have phototoxicity, since this is what PDT requires. Consequently, these are not desirable diagnostic agents.

Meanwhile, retinal circulatory microangiography using a known fluorescent dye, such as fluorescein, fluorescamin and riboflabin, has been known (U.S. Pat. No. 4,945,239). These fluorescent dyes emit fluorescence in a visible light region of 400-600 nm. In this region, the light transmission through living tissue is very low, so that the detection of lesions in the deep part of a body is nearly impossible.

In addition, the use, as fluorescent contrast agent, of cyanine compounds inclusive of indocyanine green (hereinafter to be abbreviated as ICG), which are used to determine liver function and cardiac output, has been documented (Haglund M. M. et al., *Neurosurgery*, 35, 930 (1994), Li, X. et al., *SPIE*, 2389, 789-797 (1995)). Cyanine compounds show absorbance in a near infrared light region (700-1300 nm).

Near infrared light shows high transmission through living tissues and can pass through a skull of about 10 cm in size. Because of this, it has been increasingly attracting attention in clinical medicine. For example, optical CT technique using optical transmission of medium has been drawing attention in the clinical field as a new technology. This is because near infrared light can pass through living body and can be used for monitoring oxygen concentration and circulation in the living body.

Cyanine compounds emit fluorescence in the near infrared region. The fluorescence in this region can pass through living tissues and offers the potential for a fluorescent contrast agent. Various cyanine compounds have been developed in recent years and tried as fluorescent contrast agents (WO96/17628, WP97/13490 and the like). However, an agent having sufficient solubility in water and safety to living body, as well as capability of distinguishing normal tissues from diseased tissues (selectivity for imaging target site), is not in existence.

SUMMARY OF THE INVENTION

It is therefore an object of the present invention to provide a fluorescent contrast agent. The inventive agent is low toxic and has a superior solubility in water. In addition, it emits fluorescence in a near infrared region that can pass through living tissues, and permits specific imaging of tumor and/or blood vessel.

Another object of the present invention is to provide a method of fluorescence imaging using said near infrared fluorescent contrast agent.

The present invention is predicated on the finding that introduction of three or more sulfonic acid groups into a cyanine dye compound results in the provision of a fluorescent contrast agent having a high solubility in water. It has been also found that a method of fluorescence imaging can be established when this contrast agent is used.

Thus, the present invention provides the following.

(1) A near infrared fluorescent contrast agent comprising a compound having three or more sulfonic acid groups in a molecule, which is represented by the formula [I]

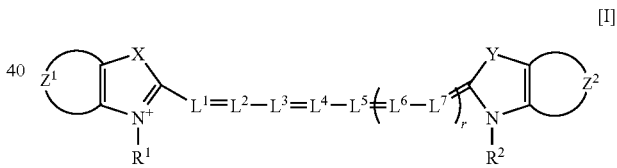

wherein $R^1$ and $R^2$ are the same or different and each is a substituted or unsubstituted alkyl; $Z^1$ and $Z^2$ are each nonmetallic atoms necessary for forming a substituted or unsubstituted condensed benzo ring or condensed naphtho ring; r is 0, 1 or 2; $L^1$-$L^7$ are the same or different and each is a substituted or unsubstituted methine, provided that when r is 2, $L^6$ and $L^7$ that occur in duplicate are the same or different; and X and Y are the same or different and each is a group of the formula

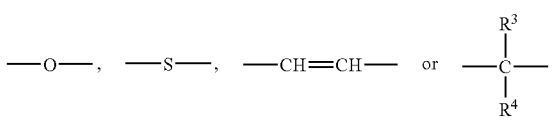

wherein $R^3$ and $R^4$ are the same or different and each is substituted or unsubstituted alkyl, or a pharmaceutically acceptable salt thereof.

(2) The near infrared fluorescent contrast agent of (1) above, which is free of a carboxylic acid group in a molecule.

(3) The near infrared fluorescent contrast agent of (1) or (2) above, wherein, in the formula [I], r is 1.

(4) The near infrared fluorescent contrast agent of any of (1) to (3) above, wherein 4 or more sulfonic acid groups are contained in a molecule.

(5) The near infrared fluorescent contrast agent of any of (1) to (4) above, wherein 10 or less sulfonic acid groups are contained in a molecule.

(6) The near infrared fluorescent contrast agent of any of (1) to (4) above, wherein 8 or less sulfonic acid groups are contained in a molecule.

(7) The near infrared fluorescent contrast agent of any of (1) to (6) above, wherein the pharmaceutically acceptable salt is a sodium salt.

(8) The near infrared fluorescent contrast agent of any of (1) to (7) above, that is for tumor imaging and/or angiography.

(9) A sodium salt of a compound of the formula [II] having three or more sulfonic acid groups in a molecule

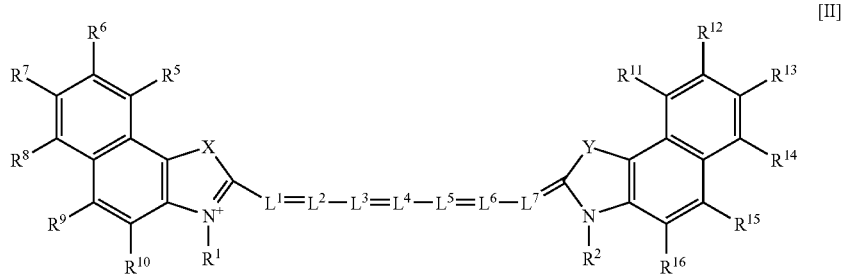

wherein $R^1$, $R^2$, $L^1$-$L^7$, X and Y are as defined above, and $R^5$ to $R^{16}$ are the same or different and each is a hydrogen atom, a sulfonic acid group, a carboxyl group, a hydroxyl group, an alkyl(sulfoalkyl)amino group, a bis(sulfoalkyl)amino group, a sulfoalkoxy group, a (sulfoalkyl)sulfonyl group or a (sulfoalkyl)aminosulfonyl group, exclusive of the groups of the following formulas

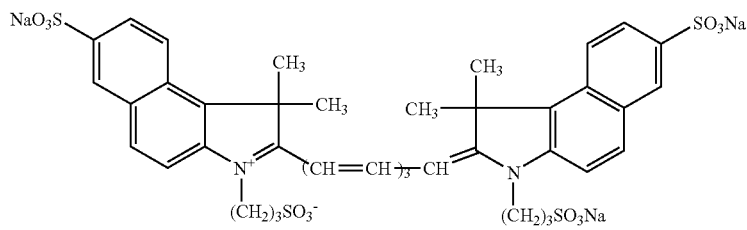

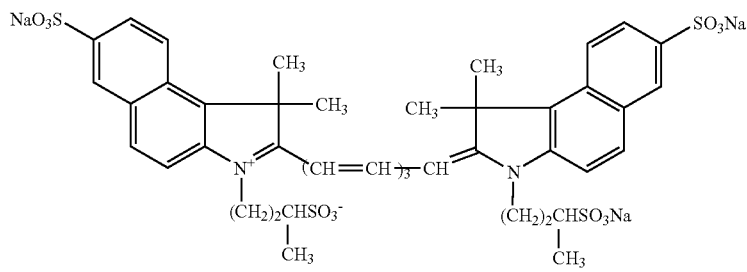

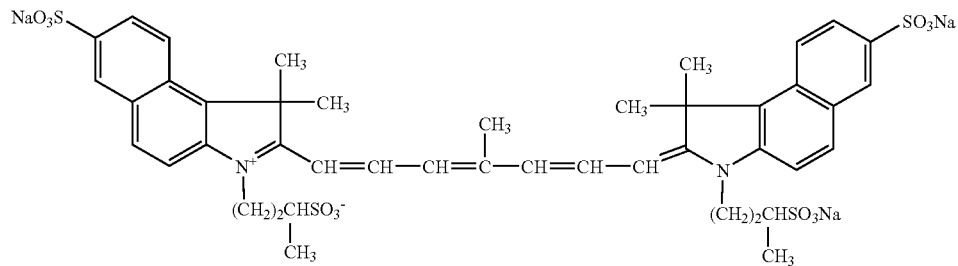
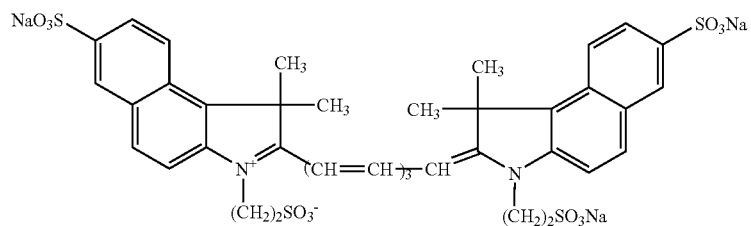
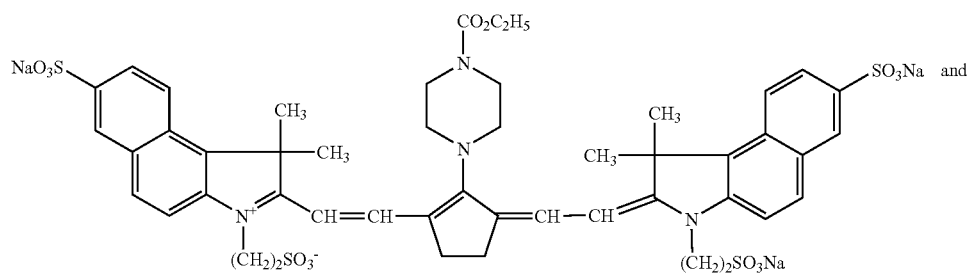
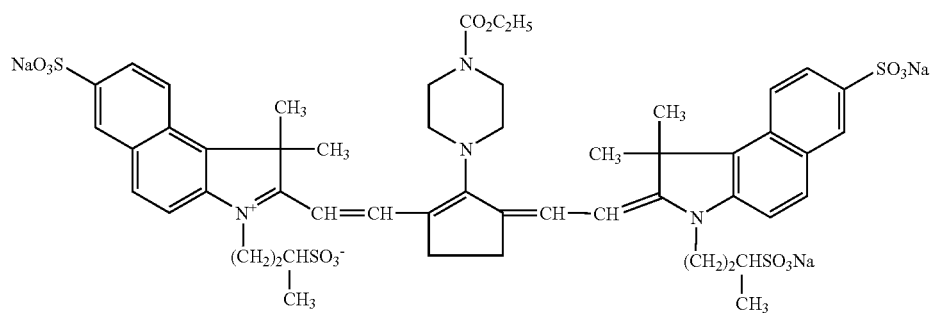

(10) The sodium salt of (9) above, wherein, in the formula [II], $R^1$ and $R^2$ are each a lower alkyl having 1 to 5 carbon atoms substituted by a sulfonic acid

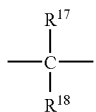

group and X and Y are the same or different and each is a group of the formula wherein $R^{17}$ and $R^{18}$ are unsubstituted lower alkyl having 1 to 5 carbon atoms.

(11) The sodium salt of (10) above, having the formula

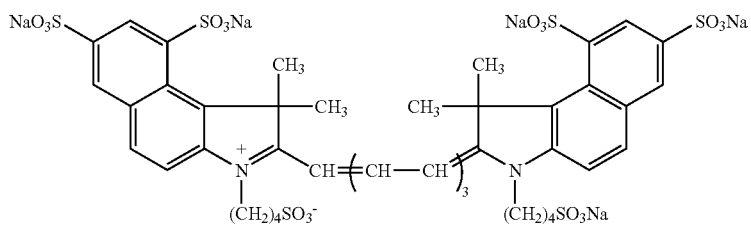

(12) A sodium salt of a compound of the formula [III-1] having three or more

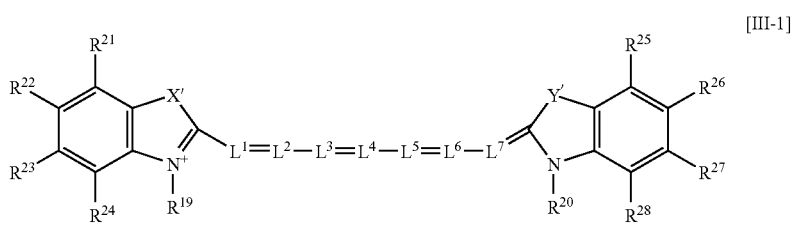

sulfonic acid groups in a molecule wherein $L^1$-$L^7$ are as defined above, $R^{19}$ and $R^{20}$ are lower alkyl having 1 to 5 carbon atoms and substituted by sulfonic acid group, $R^{21}$-$R^{28}$ are the same or different and each is hydrogen atom, sulfonic acid group, carboxyl group, hydroxyl group, alkyl(sulfoalkyl)amino group, bis(sulfoalkyl)amino group,

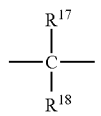

sulfoalkoxy group, (sulfoalkyl)sulfonyl group or (sulfoalkyl)aminosulfonyl group, and X' and Y' are the same or different and each is a group of the formula wherein $R^{17}$ and $R^{18}$ are as defined above, exclusive of the groups of the following formulas

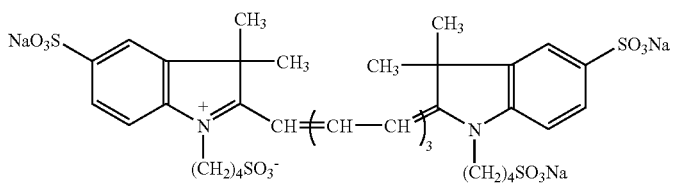

-continued

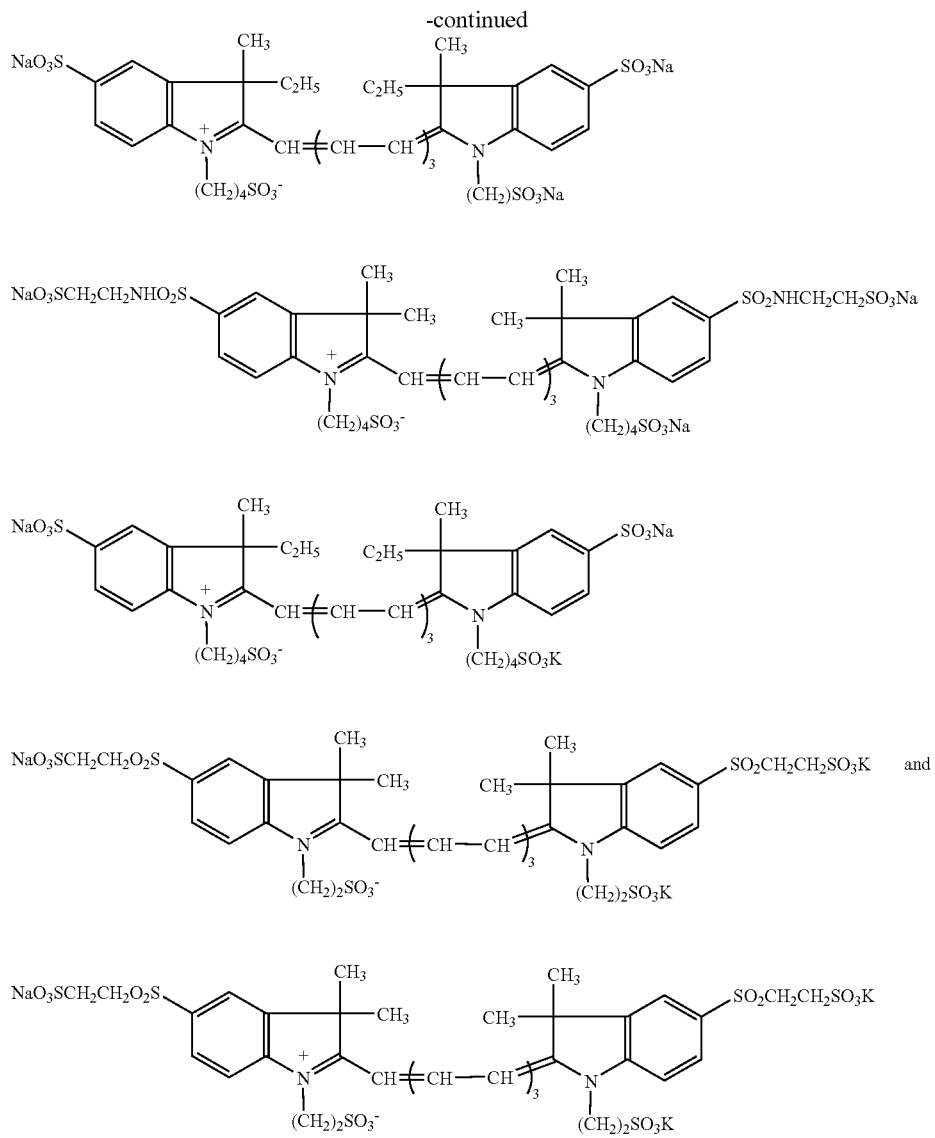

(13) The sodium salt of (12) above, wherein, in the formula [III-1], $L_4$ is methine substituted by alkyl having 1 to 4 carbon atoms.

(14) The sodium salt of (12) above, which is a sodium salt of the compound of the formula [III-2] having three or more sulfonic acid groups in a molecule

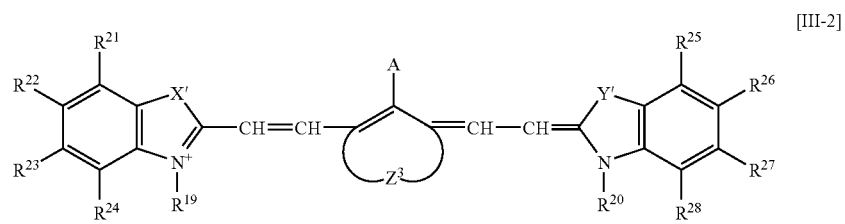

wherein $R^{19}$-$R^{28}$, X' and Y' are as defined above, $Z^3$ is a non-metallic atom group necessary for forming a 5- or 6-membered ring and A is hydrogen atom or a monovalent group.

(15) The sodium salt of (14) above, having the formula

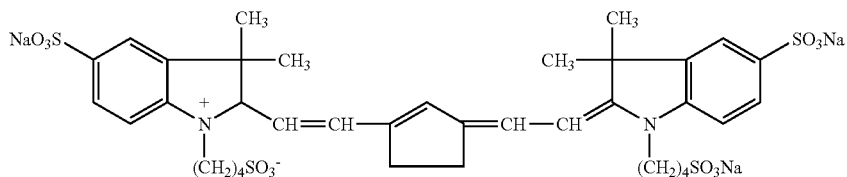

(16) The sodium salt of (12) above, having the formula

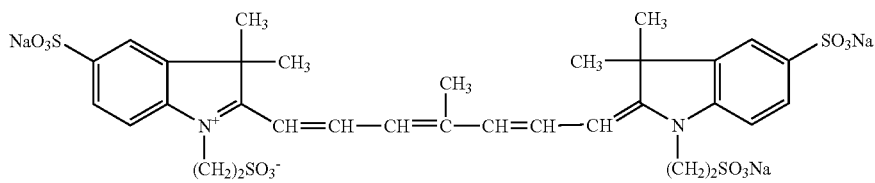

(17) The sodium salt of any of (9), (10), (12), (13) and (14) above, comprising 4 or more sulfonic acid groups in a molecule.

(18) The sodium salt of any of (9), (10), (12), (13), (14) and (17) above, comprising 10 or less sulfonic acid groups in a molecule.

(19) The sodium salt of any of (9), (10), (12), (13), (14) and (17) above, comprising 8 or less sulfonic acid groups in a molecule.

(20) A near infrared fluorescent contrast agent comprising the sodium salt of any of (9) to (19) above.

(21) The near infrared fluorescent contrast agent of (20) above, which is for tumor imaging and/or angiography.

(22) A method of fluorescence imaging comprising introducing the near infrared fluorescent contrast agent of (1) above into a living body, exposing the body to an excitation light, and detecting near infrared fluorescence from the contrast agent.

(23) The sodium salt of (9) above, which is at least one member selected from the group consisting of the compounds of the following formulas

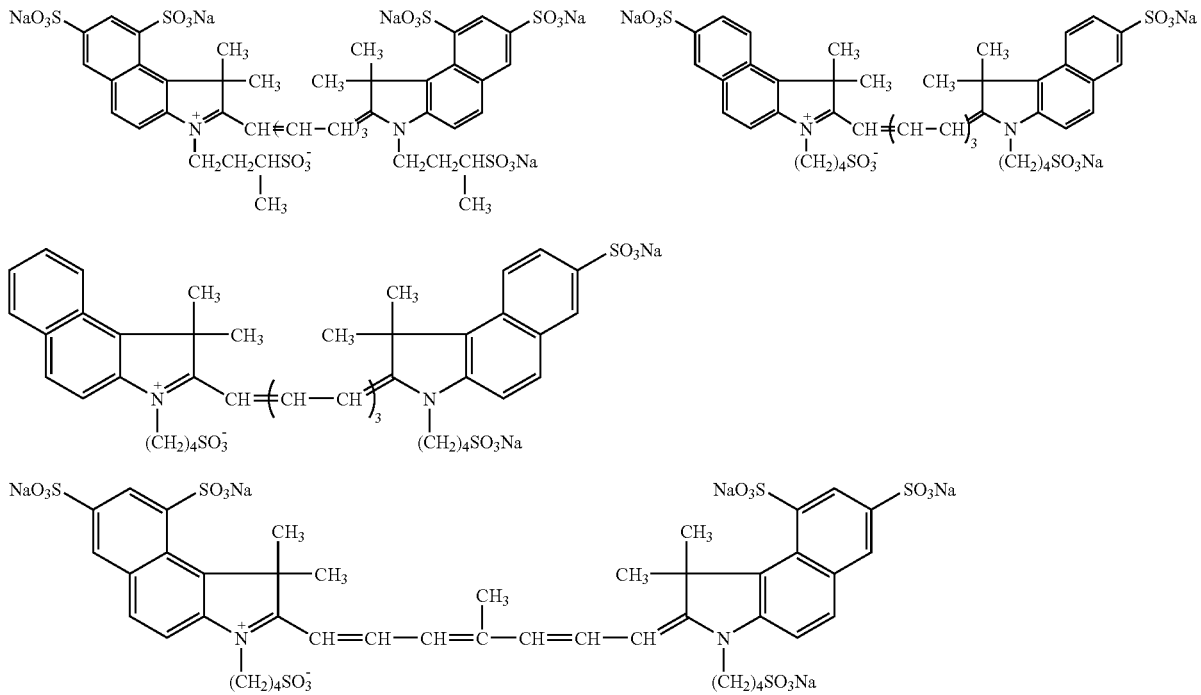

-continued
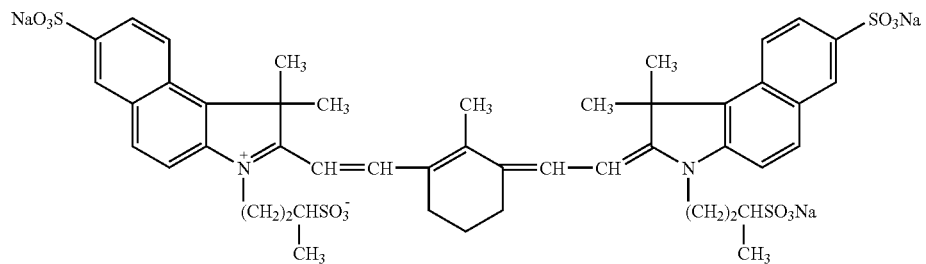
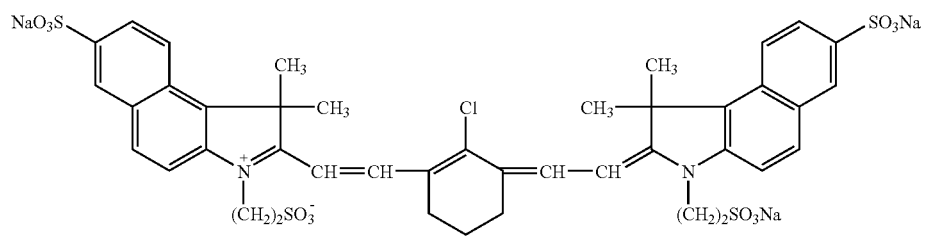
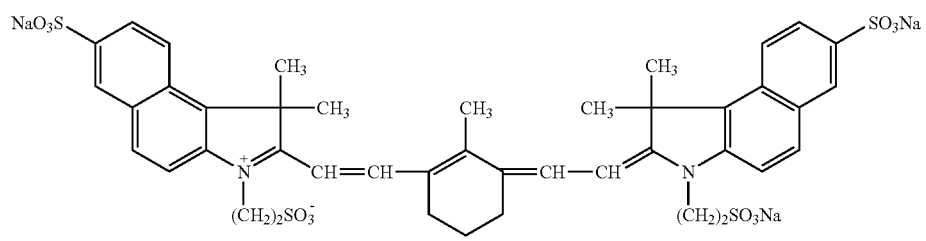
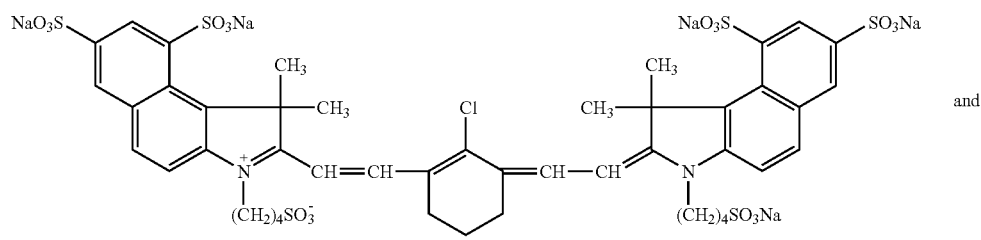
and
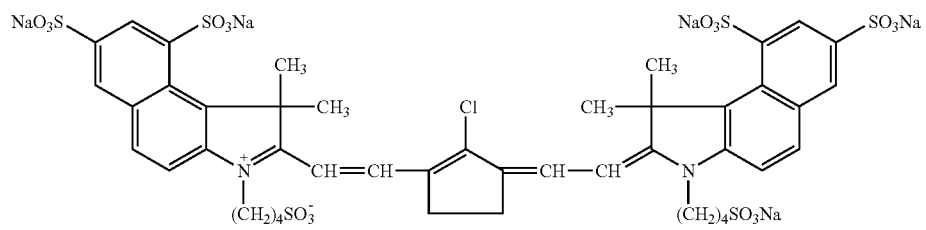

(24) The sodium salt of (12) above, which is at least one member selected from the group consisting of the compounds of the following formulas
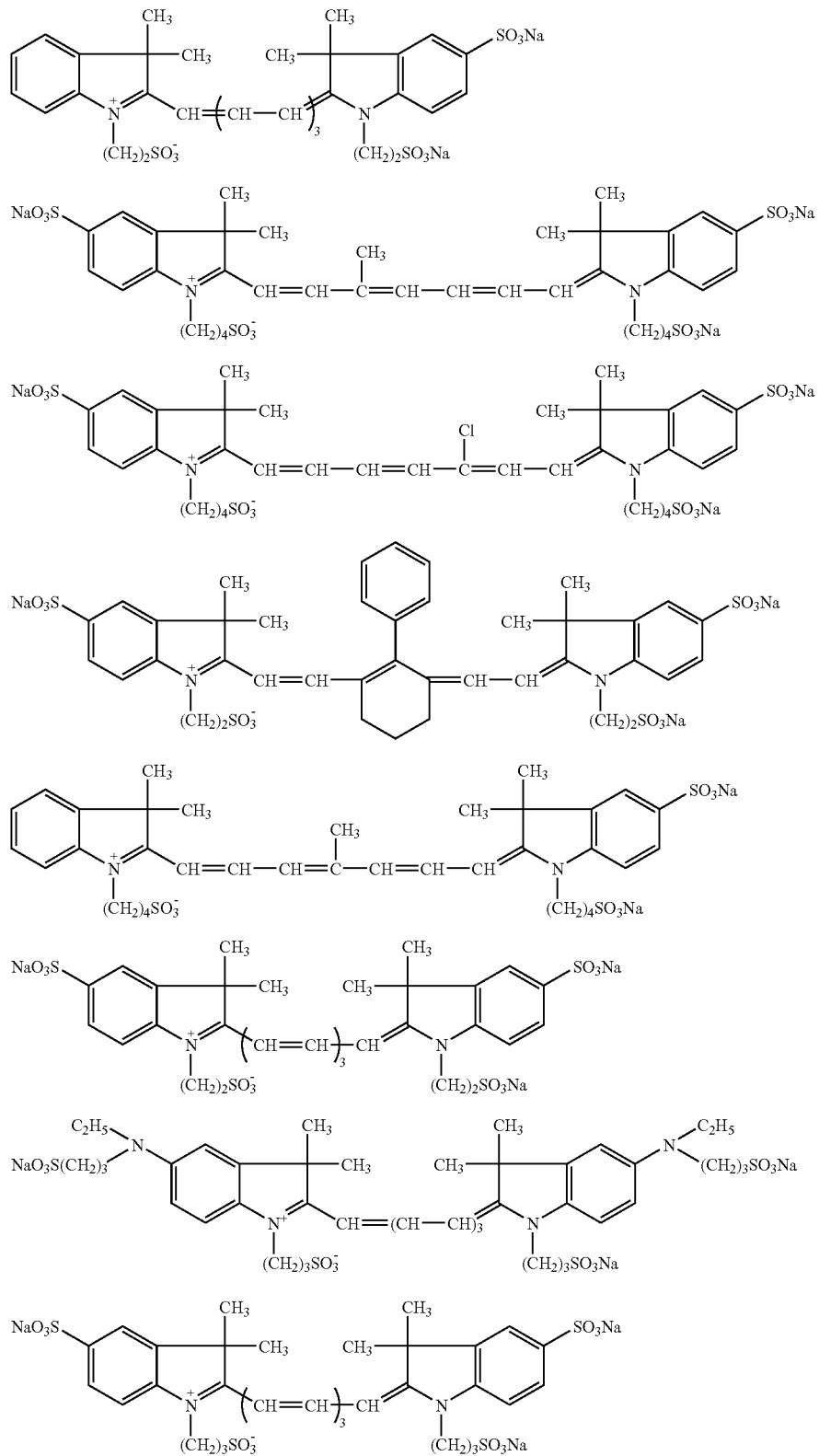

-continued
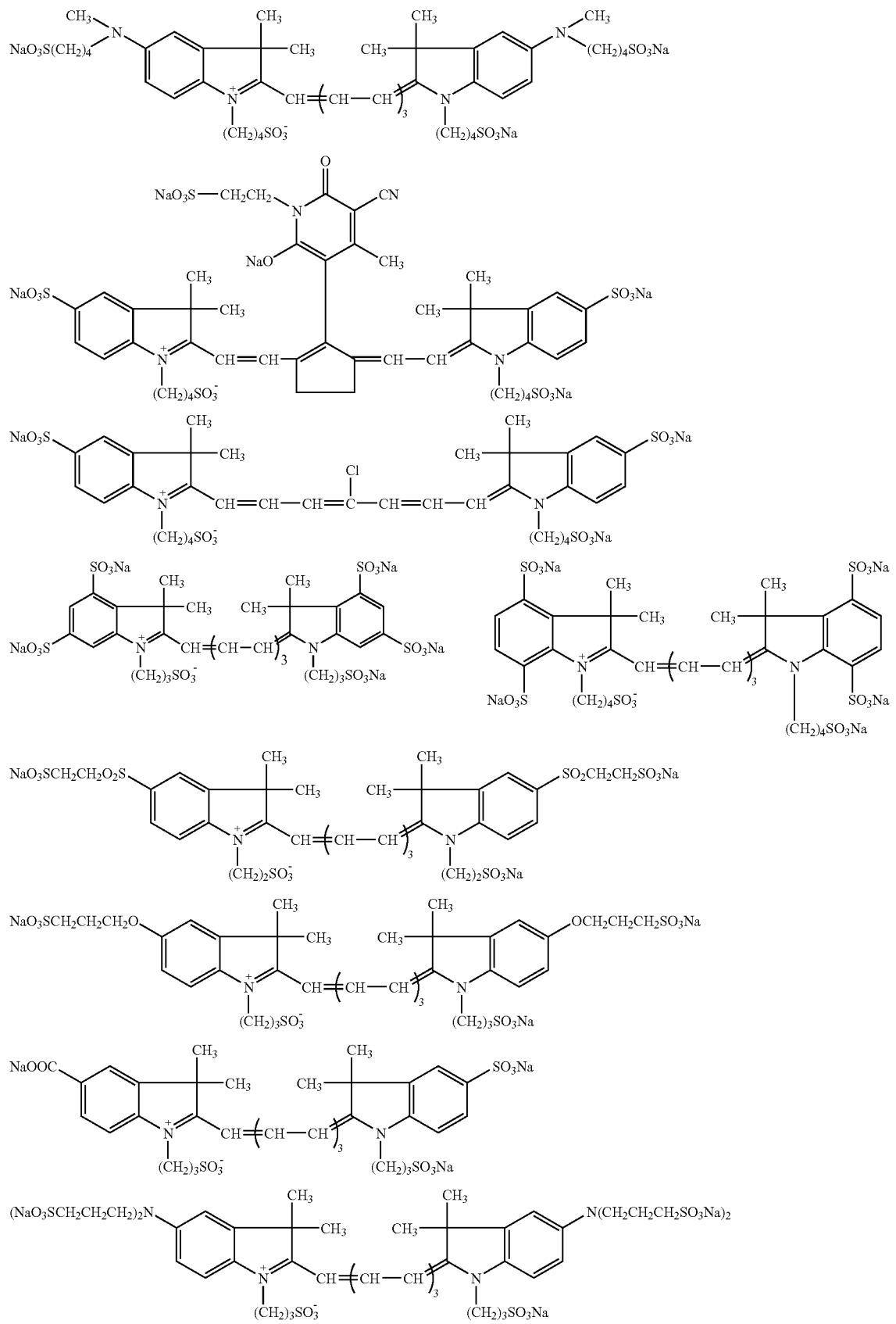

-continued
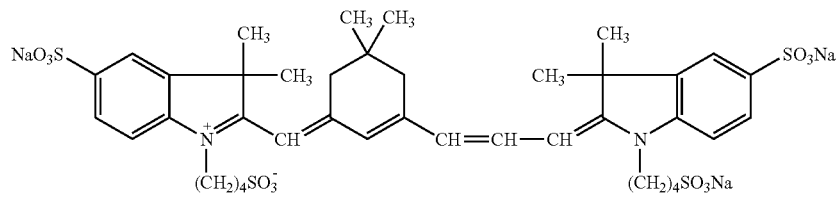
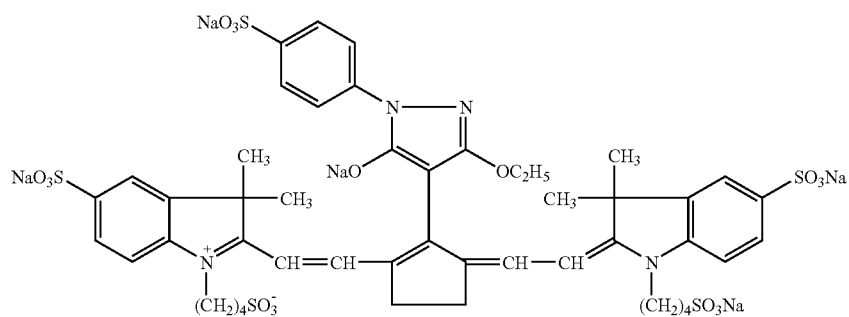
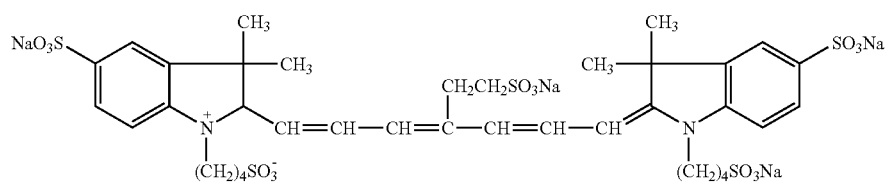
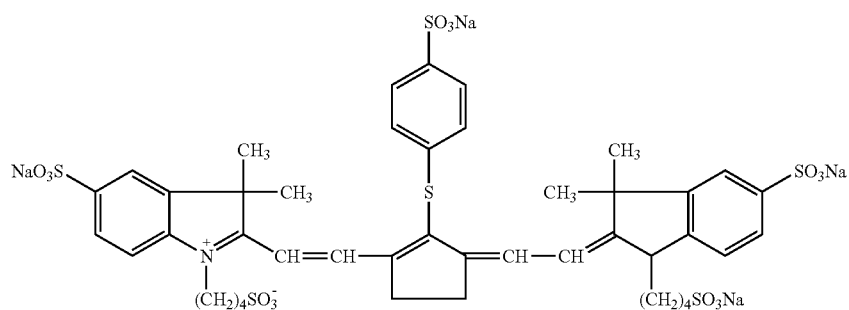
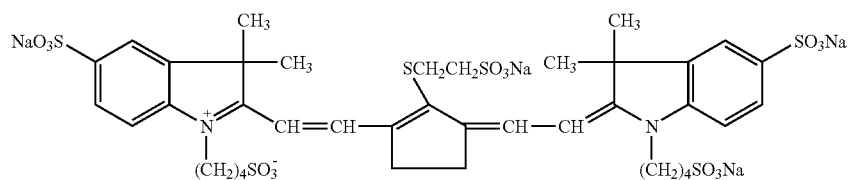
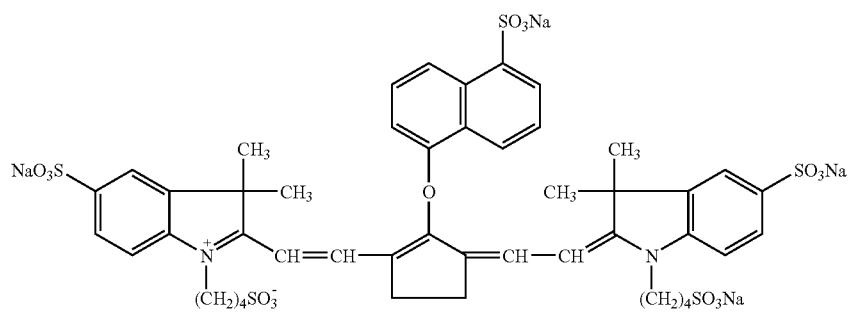

-continued
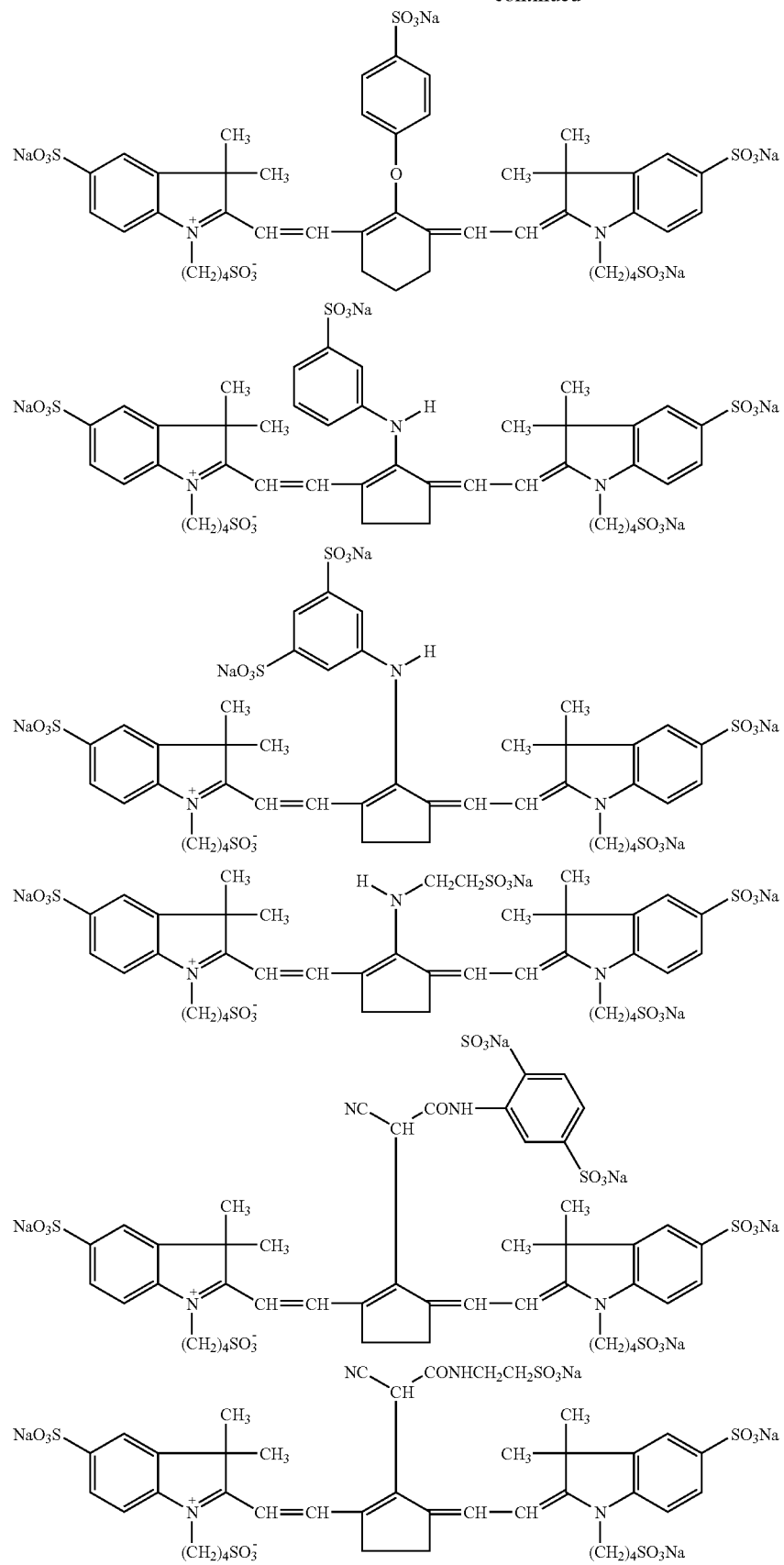

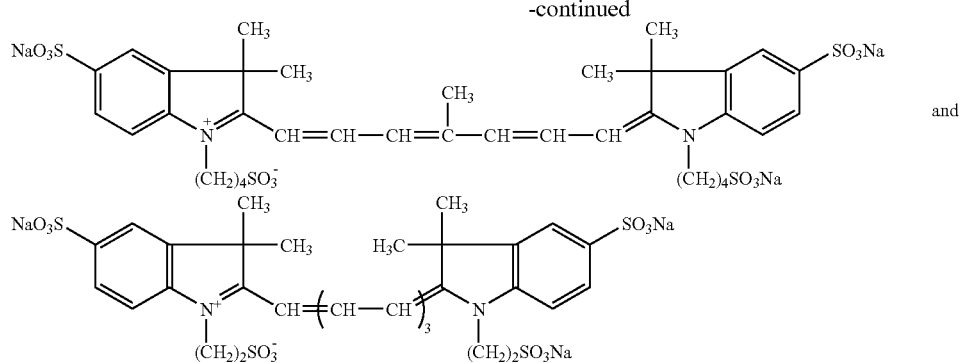
and
(25) The near infrared fluorescent contrast agent of (1) above, comprising at least one compound selected from the group consisting of the compounds of the following formulas
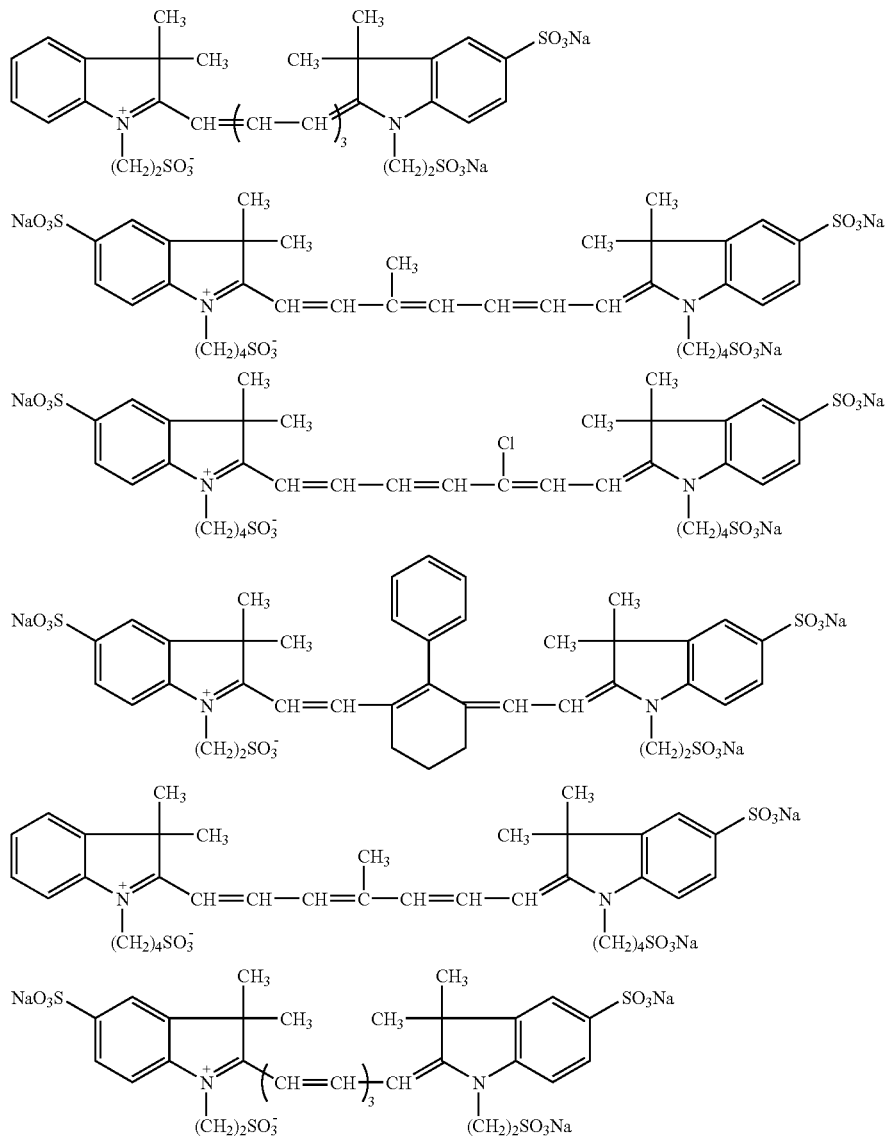

-continued
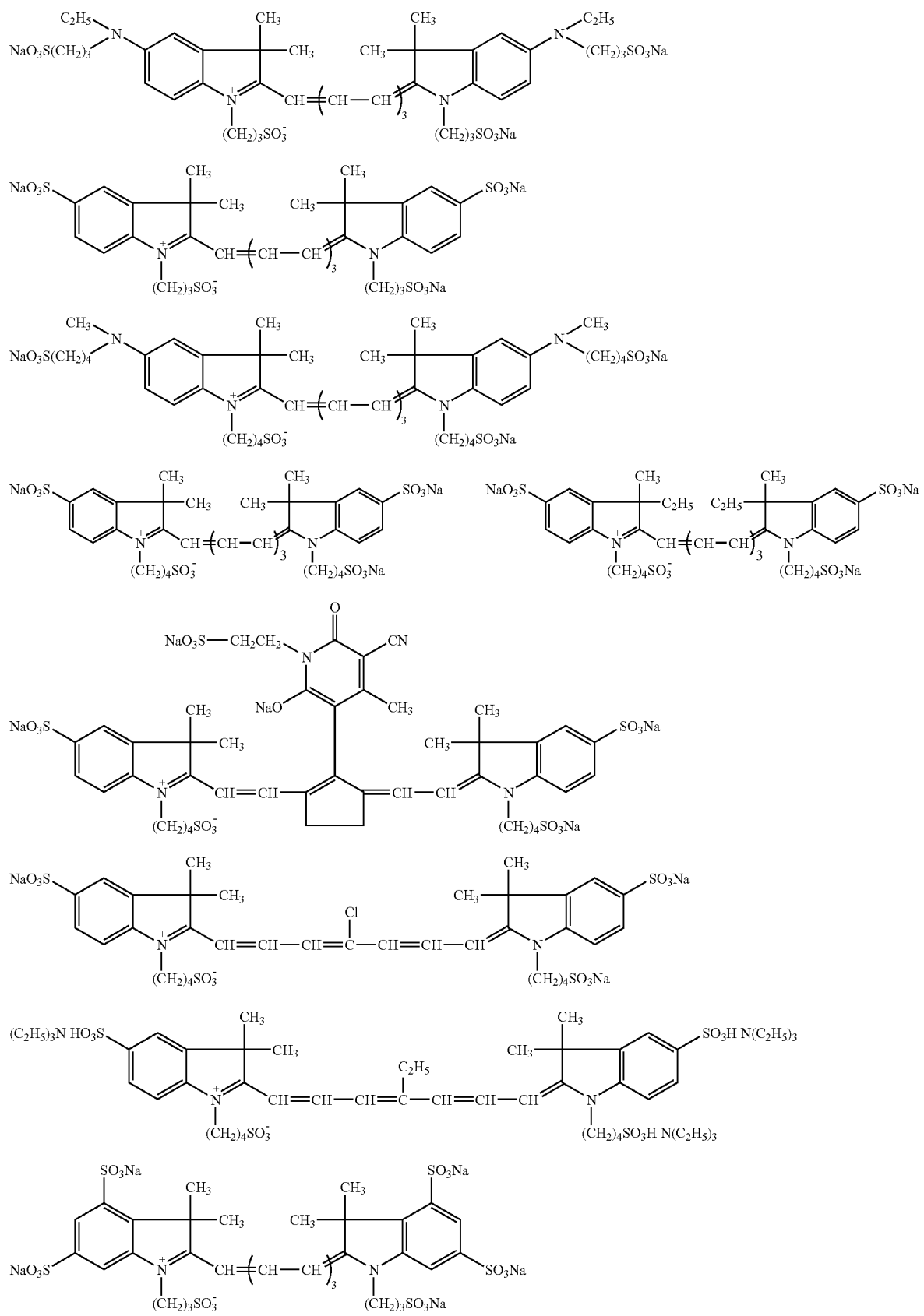

-continued
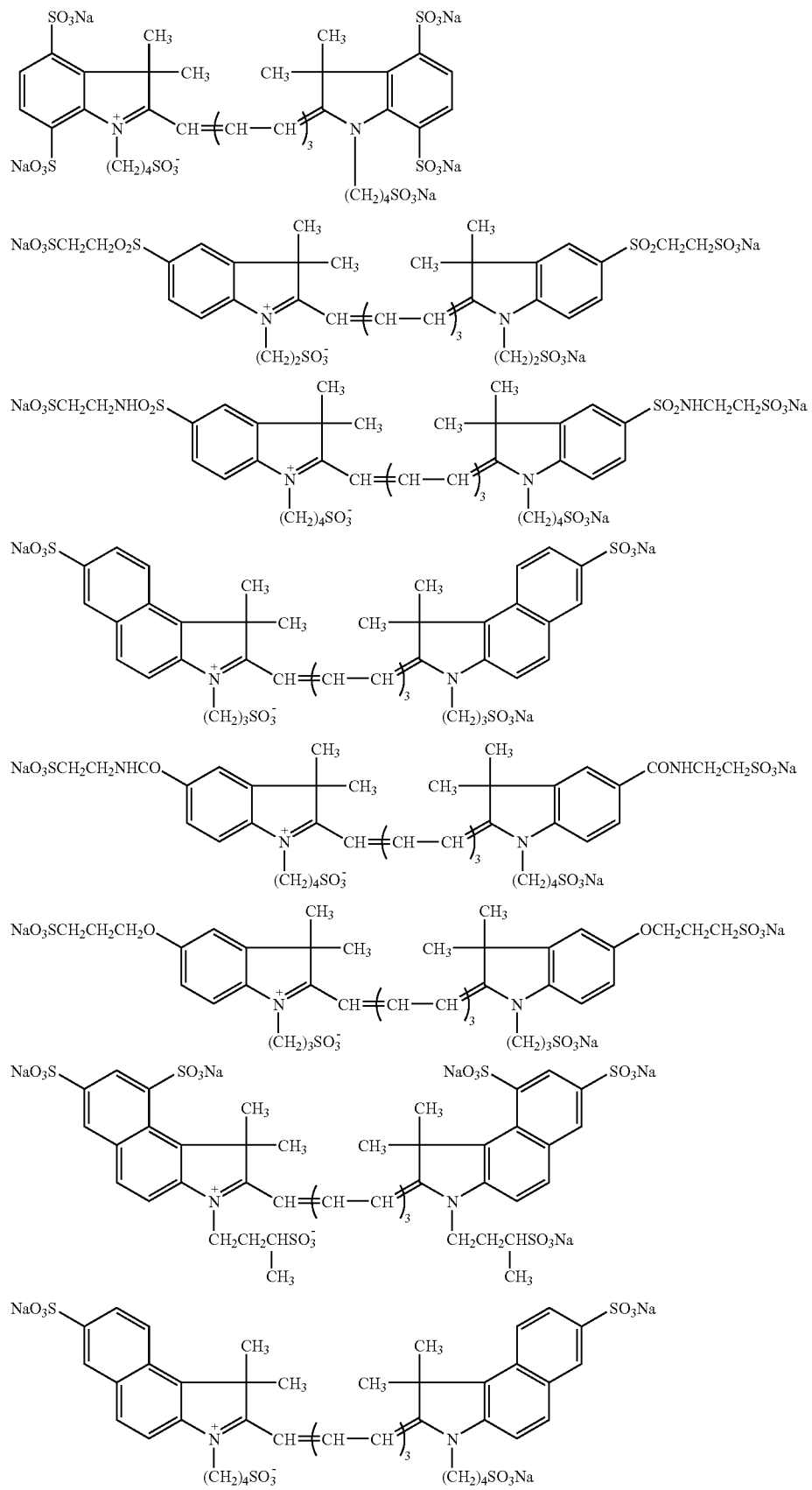

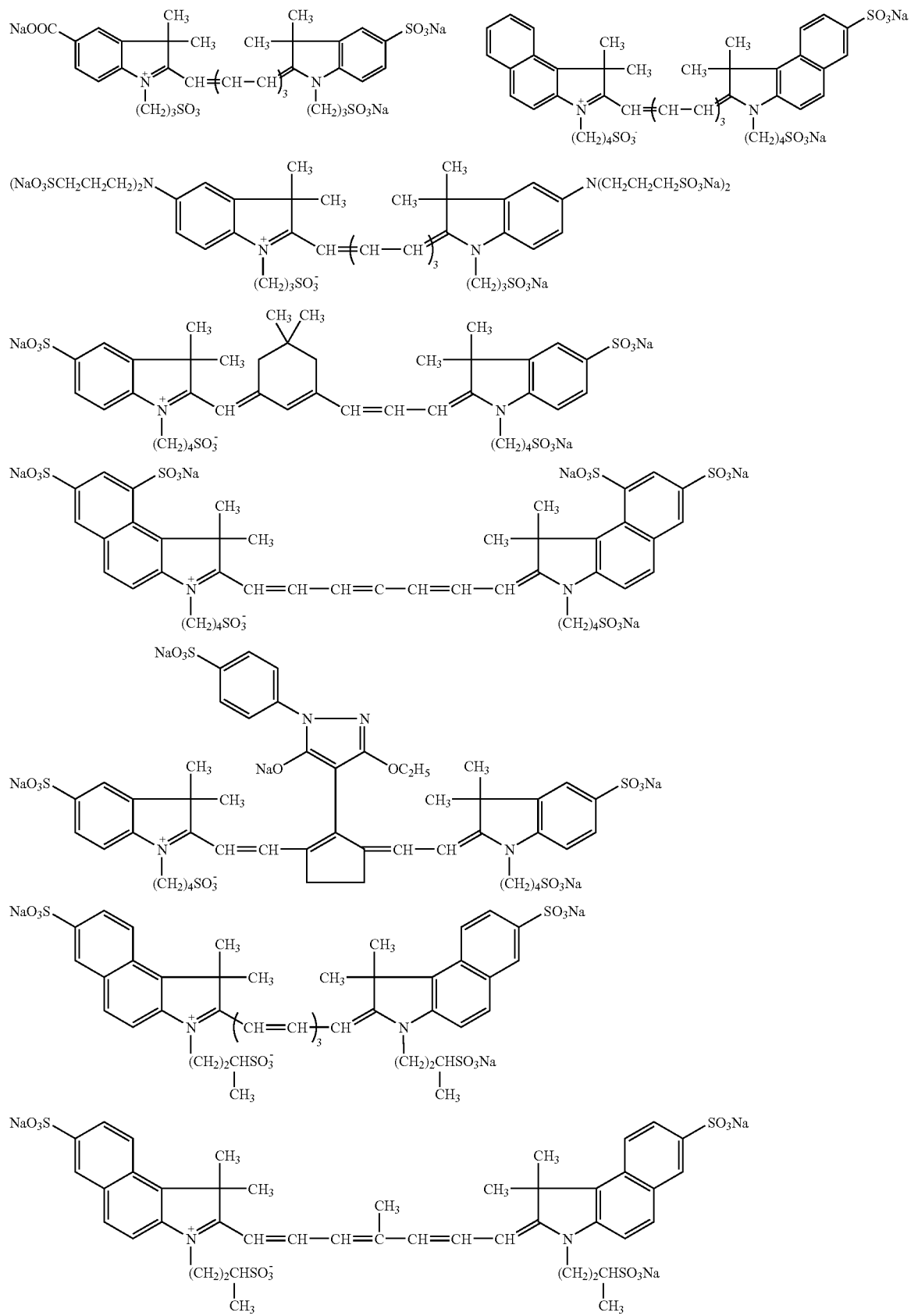

-continued
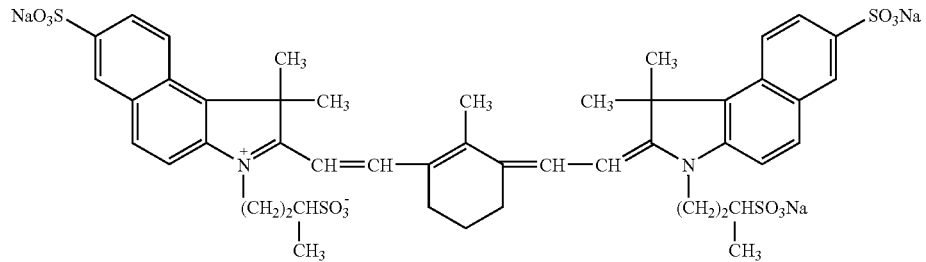
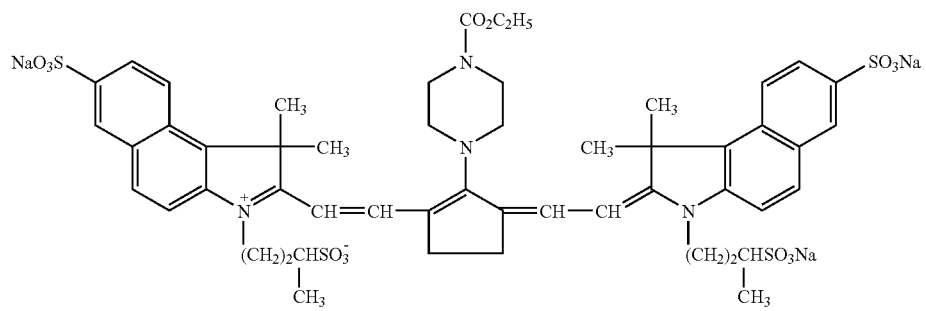
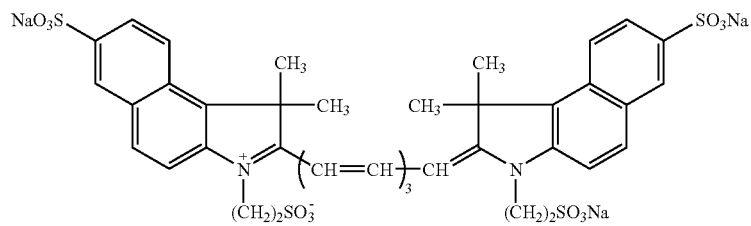
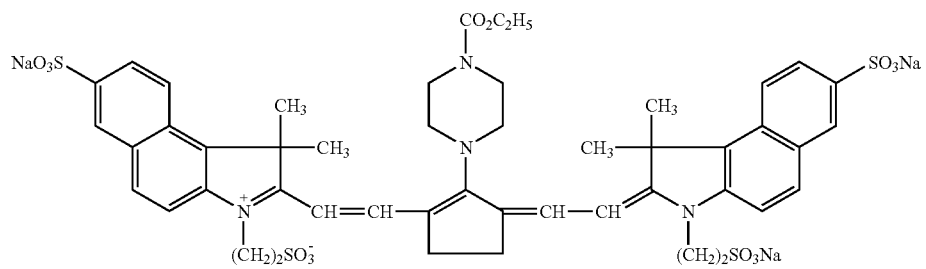
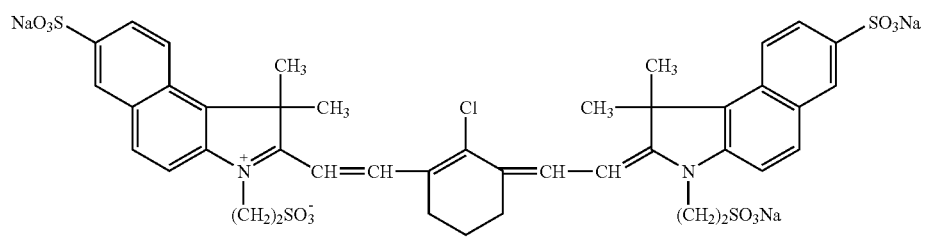
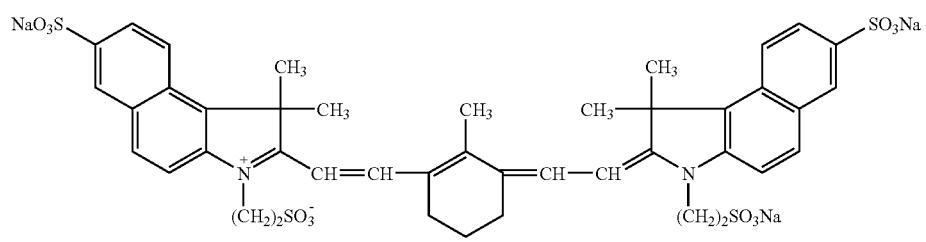

-continued
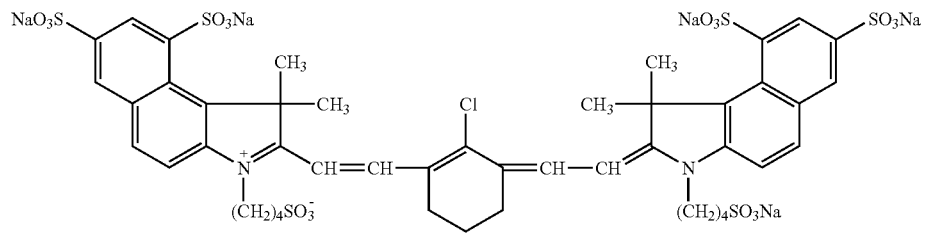
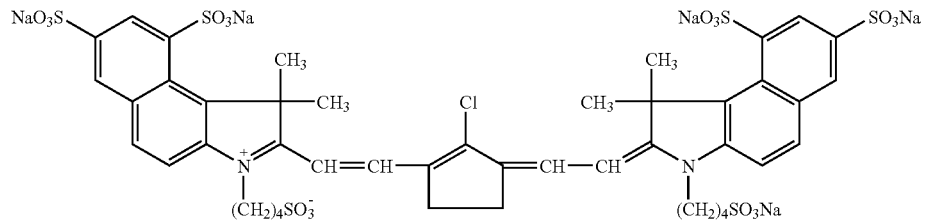
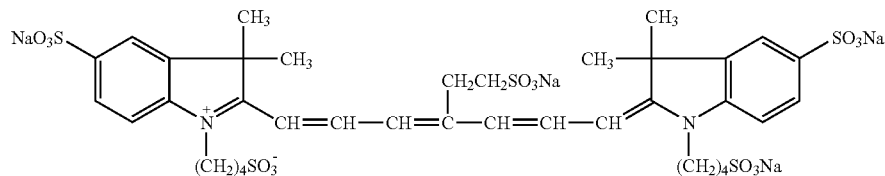
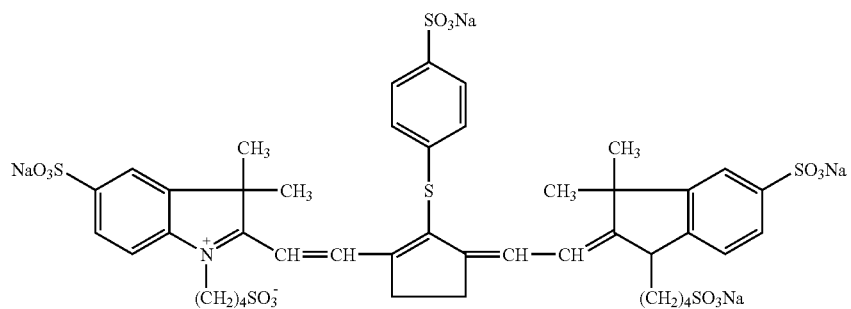
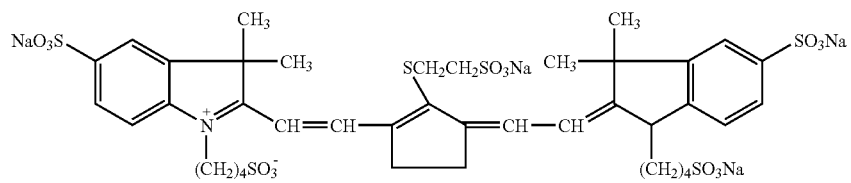
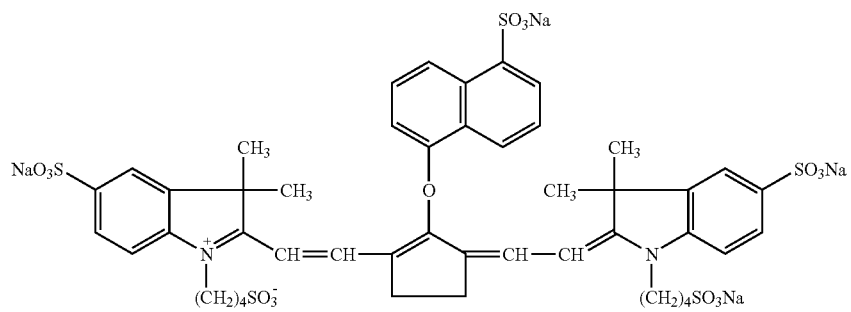

-continued
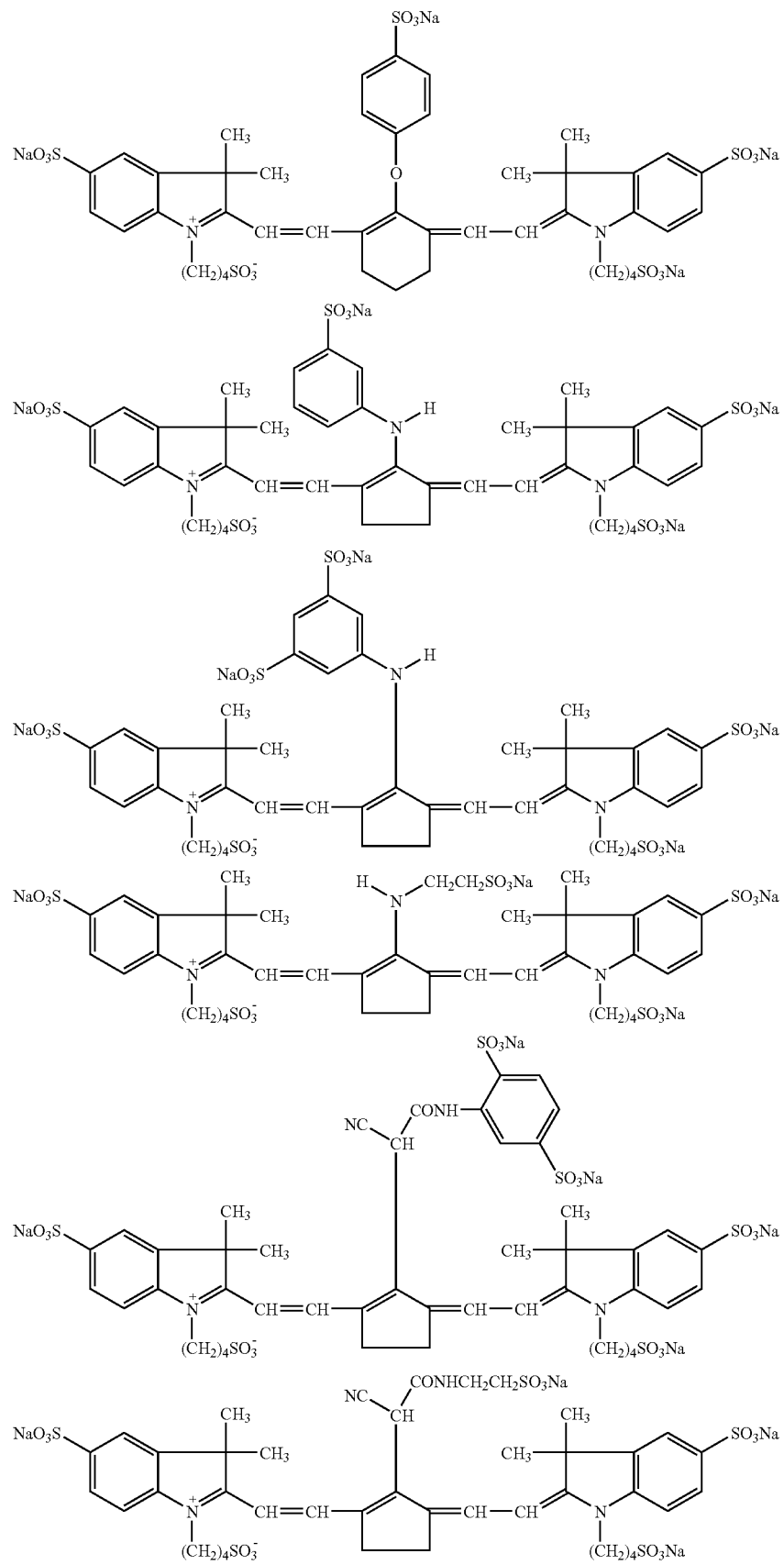

-continued

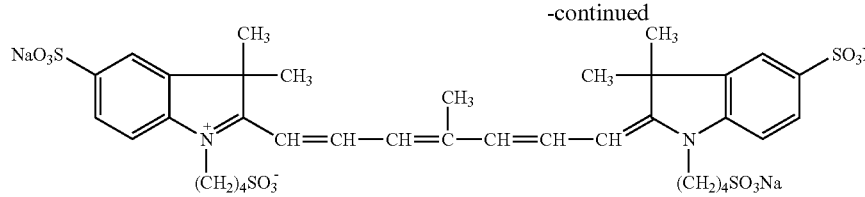

and

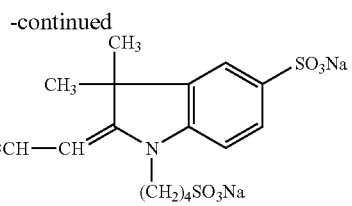

(26) The sodium salt of (14) above, wherein the monovalent group of A is substituted or unsubstituted alkyl, substituted or unsubstituted aryl, substituted or unsubstituted aralkyl, lower alkoxy, optionally substituted amino, alkylcarbonyloxy, substituted or unsubstituted alkylthio, substituted or unsubstituted arylthio, cyano, nitro or halogen atom.

DETAILED DESCRIPTION OF THE INVENTION

Figure 1:
FIGS. 1 to 4 are photographs showing fluorescence imaging at 24 hours after administration of the compound, wherein administered were A:ICG (5 mg/kg), B:NK-1967 (5 mg/kg), C:compound (29) (0.5 mg/kg) and D:compound (6) K salt (5 mg/kg).
Figure 2:
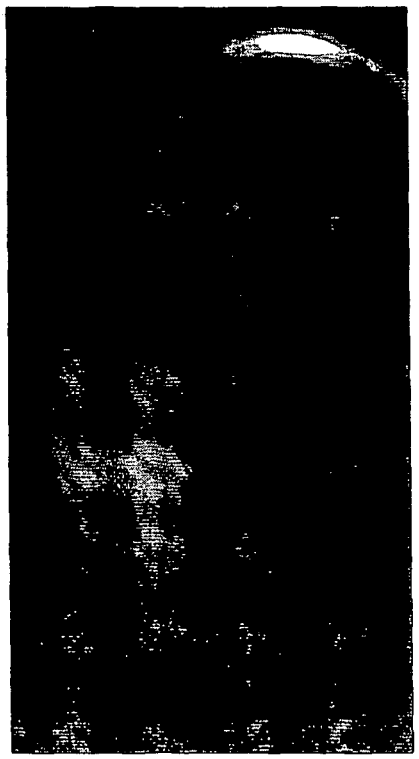
Figure 3:
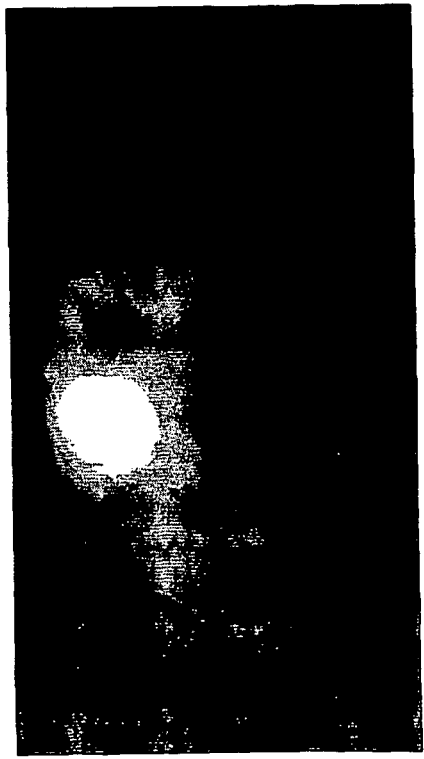
Figure 4:
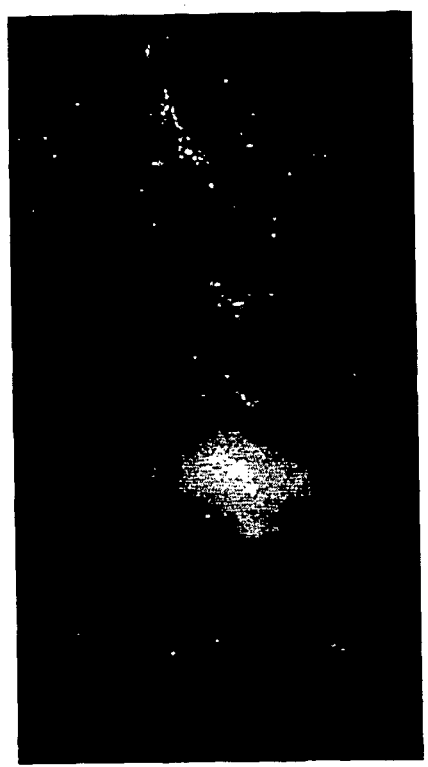
Figure 5:
FIG. 5 is a photograph showing fluorescence imaging at 24 hours after administration of the compound, wherein administered was E:compound (31) (5 mg/kg).
Figure 7:
FIGS. 6 to 9 are photographs showing fluorescence imaging at 20 seconds and 5 minutes after administration of the compound (5 mg/kg), wherein administered were A:ICG (20 seconds later), B:ICG (5 minutes later), C:compound (29) (20 seconds later) and D:compound (29) (5 minutes later).
Figure 9:
Figure 6:
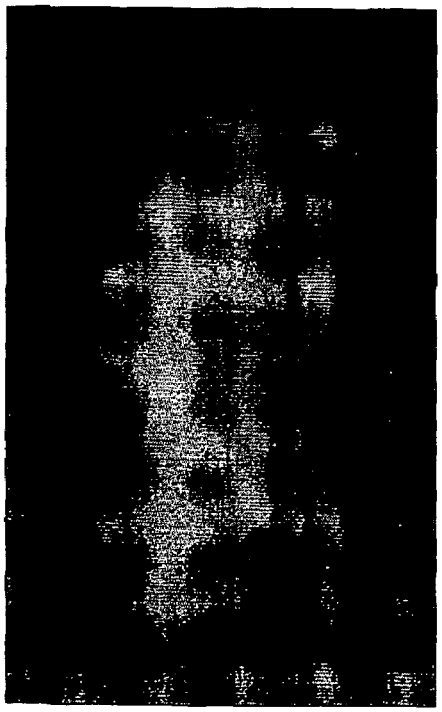
Figure 8:
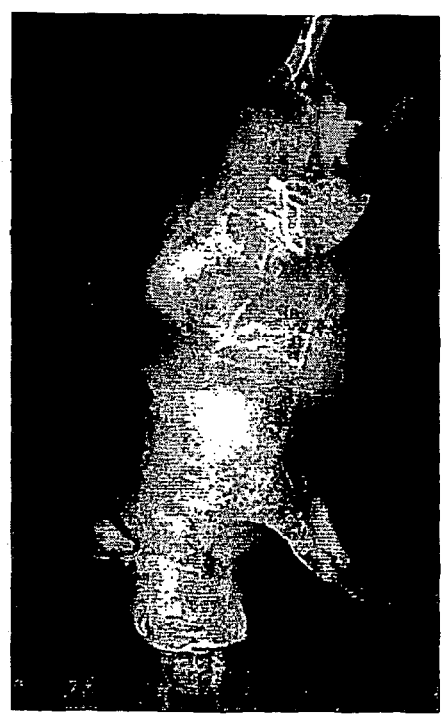

The terms used in the present specification are defined in the following.

The near infrared fluorescent contrast agent in the present invention means a contrast agent that emits fluorescence in a near infrared region.

In the present invention, the sulfonic acid group may mean sulfonate ($—SO_3^-$) when said sulfonic acid group is used to form an inner salt. In the present invention, preferable X and Y are of the following formula

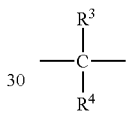

wherein $R^3$ and $R^4$ are the same or different and each is substituted or unsubstituted alkyl.

The alkyl of "substituted or unsubstituted alkyl" at $R^1$, $R^2$, $R^3$ and $R^4$ is preferably linear or branched lower alkyl having 1 to 5 carbon atoms, such as methyl, ethyl, propyl, isopropyl, butyl, isobutyl, sec-butyl, tert-butyl, pentyl, isopentyl, neopentyl, tert-pentyl, 2-methylpropyl, 1,1-dimethylpropyl and the like. The substituent may be, for example, sulfonic acid group, carboxyl, hydroxy and the like. Examples of substituted alkyl include hydroxymethyl, 1-hydroxyethyl, 2-hydroxyethyl, 2-hydroxypropyl, 3-hydroxypropyl, 4-hydroxybutyl, carboxymethyl, carboxyethyl, carboxybutyl, sulfomethyl, 2-sulfoethyl, 3-sulfopropyl, 4-sulfobutyl and the like. Preferred $R^1$ and $R^2$ are lower alkyl having 1 to 5 carbon atoms that is substituted by sulfonic acid group (e.g., 2-sulfoethyl, 3-sulfopropyl, 4-sulfobutyl and the like), and $R^3$ and $R^4$ are unsubstituted lower alkyl having 1 to 5 carbon atoms (e.g., methyl, ethyl and the like).

The unsubstituted lower alkyl having 1 to 5 carbon atoms at $R^{17}$ and $R^{18}$ is exemplified by those mentioned above with regard to the alkyl of "substituted or unsubstituted alkyl" at $R^1$, $R^2$, $R^3$ and $R^4$.

The alkyl group of the lower alkyl having 1 to 5 carbon atoms that is substituted by sulfonic acid group at $R^{19}$ and $R^{20}$ is exemplified by those mentioned above with regard to the alkyl of "substituted or unsubstituted alkyl" at $R^1$, $R^2$, $R^3$ and $R^4$, and examples of the substituted lower alkyl having 1 to 5 carbon atoms include 2-sulfoethyl, 3-sulfopropyl and 4-sulfobutyl.

The alkyl moiety of alkyl(sulfoalkyl)amino group, bis(sulfoalkyl)amino group, sulfoalkoxy group, (sulfoalkyl)sulfonyl group and (sulfoalkyl)aminosulfonyl group at $R^{21}$-$R^{28}$ is preferably a linear or branched lower alkyl having 1 to 5 carbon atoms, which is exemplified by those mentioned above with regard to the alkyl of "substituted or unsubstituted alkyl" at $R^1$, $R^2$, $R^3$ and $R^4$.

In the present invention, the "nonmetallic atoms necessary for forming a substituted or unsubstituted condensed benzo ring or condensed naphtho ring" means a bonding group necessary for forming a condensed benzo ring or condensed naphtho ring, which is a group of the formula

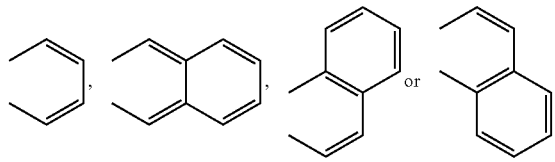

When the condensed benzo ring or condensed naphtho ring has a substituent, said bonding group may include a substituent.

Specific examples thereof include carbon atom, nitrogen atom, oxygen atom, hydrogen atom, sulfur atom, halogen atom (e.g., fluorine atom, chlorine atom, bromine atom and iodine atom) and the like.

The substituent of the condensed benzo ring and condensed naphtho ring formed by the nonmetallic atoms at $Z^1$ and $Z^2$ is exemplified by sulfonic acid group, carboxyl, hydroxy, halogen atom (e.g., fluorine atom, chlorine atom, bromine atom and iodine atom), cyano, substituted amino (e.g., dimethylamino, diethylamino, ethyl 4-sulfobutylamino, di-(3-sulfopropyl)amino and the like), and substituted or unsubstituted alkyl as defined above, which is bonded to the ring directly or via a divalent bonding group. Preferable divalent bonding group may be, for example, —O—, —NHCO—, —NHSO$_2$—, —NHCOO—, —NHCONH—, —COO—, —CO—, SO$_2$—, and the like. The alkyl of substituted or unsubstituted alkyl that is bonded to the ring directly or via a divalent connection group is exemplified preferably by methyl, ethyl, propyl and butyl, and the substituent is preferably exemplified by sulfonic acid group, carboxyl and hydroxy.

The substituent of methine at $L^1$-$L^7$ is exemplified by substituted or unsubstituted alkyl (defined above), halogen atom (defined above), substituted or unsubstituted aryl, lower alkoxy and the like. The aryl of "substituted or unsubstituted aryl" is exemplified by phenyl, naphthyl and the like, preferably phenyl. Examples of the substituent include halogen atom (defined above, preferably chlorine atom) and the like. The substituted aryl includes, for example, 4-chlorophenyl and the like. The lower alkoxy is preferably linear or branched alkoxy having 1 to 6 carbon atoms, which is specifically methoxy, ethoxy, propoxy, butoxy, tert-butoxy, pentyloxy and the like, preferably methoxy and ethoxy. In addition, the substituents of methine at $L^1$-$L^7$ may be bonded each other to form a ring containing three methine groups, and this ring may further form a condensed ring with a ring containing different methine group. The ring containing three methine groups that is formed by the bonding of the substituents of methine at $L^1$-$L^7$ is exemplified by 4,4-dimethylcyclohexene ring and the like.

The conjugated methine chain consisting of the groups of $L^1$-$L^7$, and having a ring is preferably the group of the formula (a):

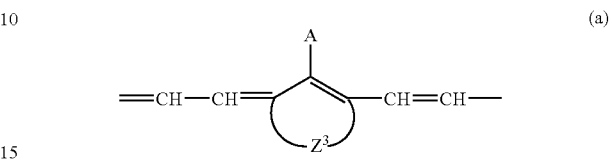

wherein $Z^3$ denotes nonmetallic atoms necessary to form a 5- or 6-membered ring and A is hydrogen atom or a monovalent group.

The "nonmetallic atoms necessary to form a 5- or 6-membered ring" is exemplified by those mentioned above.

In the formula (a) and [III-2] to be mentioned later, - or 6-membered ring at $Z^3$ is exemplified by cyclopentene ring, cyclohexene ring, 4,4-dimethylcyclohexene ring and the like, with particular preference given to cyclopentene ring.

The monovalent group represented by A includes, for example, substituted or unsubstituted alkyl (defined above), substituted or unsubstituted aryl (defined above), substituted or unsubstituted aralkyl, lower alkoxy (defined above), substituted amino which is optionally substituted, alkylcarbonyloxy (e.g., acetoxy), substituted or unsubstituted alkylthio, substituted or unsubstituted arylthio, cyano, nitro, halogen atom (defined above), and the like. As used herein, aralkyl of the "substituted or unsubstituted aralkyl" is exemplified by benzyl, 2-phenylethyl, 1-phenylethyl, 3-phenylpropyl and the like, and the substituent may be sulfonic acid group, carboxyl, hydroxy, substituted or unsubstituted alkyl (defined above), alkoxy (defined above), halogen atom (defined above), and the like. The substituted amino of the "substituted amino which is optionally substituted" includes, for example, alkylamino (e.g., methylamino, ethylamino and the like), dialkylamino (dimethylamino, diethylamino and the like), diphenylamino, methylphenylamino, cyclic amino (e.g., morpholino, imidazolidino, ethoxycarbonylpiperadino and the like) and the like. The substituent with regard to the optional substitution of the "substituted amino which is optionally substituted" includes sulfonic acid group, carboxyl and the like. The alkylthio of the "substituted or unsubstituted alkylthio" may be, for example, methylthio, ethylthio and the like. Examples of the substituent include sulfonic acid group, carboxyl and the like. The arylthio of the "substituted or unsubstituted arylthio" is exemplified by phenylthio, naphthylthio and the like. Examples of the substituent include sulfonic acid group, carboxyl and the like.

The monovalent group represented by A is preferably fluorine atom, chlorine atom, dialkylamino (preferably having 6 or less carbon atoms, and optionally forming a ring) or morpholino. This group particularly preferably has a sulfonic acid group.

In the formula [I], r is preferably 1.

The pharmaceutically acceptable salt may be any as long as it forms a nontoxic salt with the compound of the formula [I]. Examples thereof include alkali metal salts such as sodium salt, potassium salt; salt of alkaline earth metal such as magnesium salt, calcium salt and the like; organic ammonium salt such as ammonium salt, triethyl ammonium salt, tributyl ammonium salt, pyridinium salt and the like; salt of amino acid such as lysine salt, arginine salt and the like. Particularly preferred is sodium salt causing less toxicity in the living body.

The fluorescent contrast agent to be used in a living body should be particularly water soluble. In the present invention, tuted by sulfonic acid group, and X and Y are the same or different and each is a group of the formula

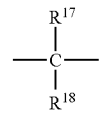

wherein $R^{17}$ and $R^{18}$ are the same or different and each is unsubstituted lower alkyl having 1 to 5 carbon atoms alkyl, said salt having three or more sulfonic acid groups in a molecule, with particular preference given to a compound of the formula

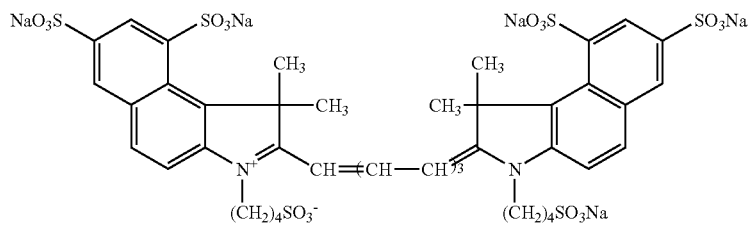

the near infrared fluorescent contrast agent has a noticeably improved water solubility by the introduction of 3 or more sulfonic acid groups into the above-mentioned compound. For superior water solubility, the number of the sulfonic acid groups is preferably 4 or more. For easy synthesis, the number of the sulfonic acid groups is not more than 10, preferably not more than 8. The improvement in the water solubility can be determined by measuring partition coefficient of each compound, which for example, may be measured in a two-phase system of butanol/water. More specifically, introduction of 3 or more sulfonic acid groups results in a partition coefficient log Po/w of n-butanol/water of not more than −1.00.

The sulfonic acid groups are particularly preferably introduced into the positions of $R^1$, $R^2$, $Z^1$ and/or $Z^2$ of the formula [I] and $R^1$, $R^2$, $R^5$, $R^7$, $R^{11}$ and/or $R^{13}$ of the formula [II].

In addition, these sulfonic acid groups are preferably introduced into $L^4$ of the conjugated methine chain at the position A of the above-mentioned formula (a) via a divalent group such as alkylene.

Of the sodium salts of compounds of the formula [II] having three or more sulfonic acid groups in a molecule, preferred is a sodium salt of a compound wherein $R^1$ and $R^2$ are lower alkyl having 1 to 5 carbon atoms which is substi- Of the compounds of the formula [I] having three or more sulfonic acid groups in a molecule and pharmaceutically acceptable salts thereof, preferred is a sodium salt of a compound of the formula [III-1]

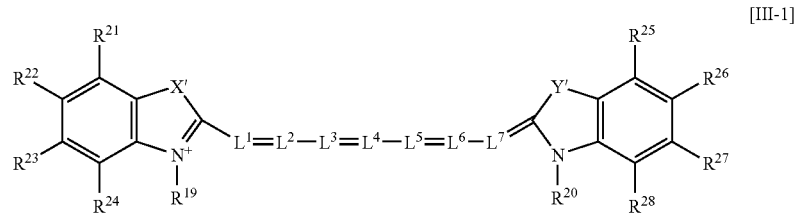

wherein $L^1$-$L^7$ are as defined above, $R^{19}$ and $R^{20}$ are lower alkyl having 1 to 5 carbon atoms which is substituted by sulfonic acid group, and $R^{21}$ to $R^{28}$ are the same or different and each is hydrogen atom, sulfonic acid group, carboxyl group, hydroxyl group, alkyl(sulfoalkyl)amino group, bis (sulfoalkyl)amino group, sulfoalkoxy group, (sulfoalkyl)sulfonyl group or (sulfoalkyl)amino-sulfonyl group, and X' and Y' are the same or different and each is a group of

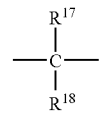

the formula wherein $R^{17}$ and $R^{18}$ are as defined above, said salt having three or more sulfonic acid groups in a molecule, with particular preference given to the compound of the following formula.

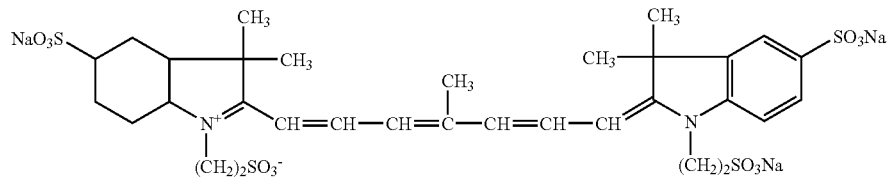

Of the sodium salts of the compounds of the formula [III-1] having three or more sulfonic acid groups in a molecule, preferred is a sodium salt of a compound of the formula [III-2]

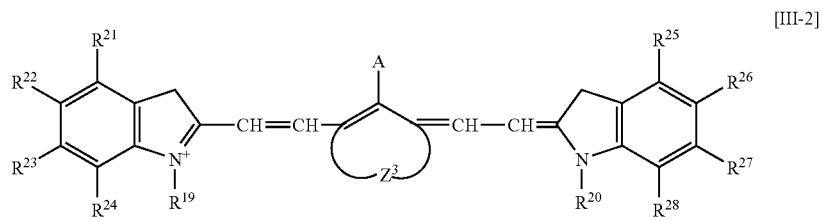

[III-2]

wherein $R^{19}$-$R^{28}$, X' and Y' are as defined above, $Z^3$ is non-metallic atoms necessary to form a 5- or 6-membered ring and A is hydrogen atom or a monovalent group, said salt having three or more sulfonic acid groups in a molecule, with particular preference given to the compound of the following formula

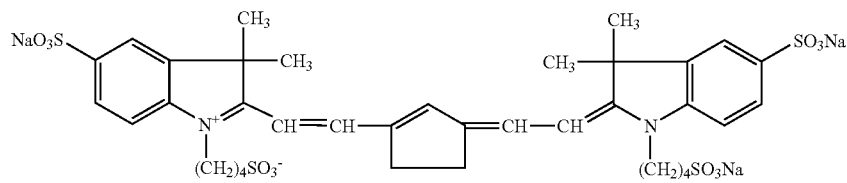

The compounds contained in the inventive near infrared fluorescent contrast agent may be any as long as it has formula [I] or [II], as well as 3 or more, preferably 4 or more, sulfonic acid groups in a molecule. These compounds can be synthesized according to a known production method of cyanine dye compounds disclosed in *The Cyanine Dyes and Related Compounds*, F. M. Hamer, John Wiley and Sons, New York, 1964, *Cytometry*, 10, 3-10 (1989), *Cytometry*, 11, 418-430 (1990), *Cytometry*, 12 723-730 (1990), *Bioconjugate Chem.* 4, 105-111 (1993), *Anal. Biochem.*, 217, 197-204 (1994), *Tetrahedron*, 45, 4845-4866 (1989), EP-A-0591820A1, EP-A-0580145A1, and the like. Alternatively, they can be semisynthesized from a commercially available cyanine dye compound by a known method. To be specific, they can be synthesized by reacting a dianyl compound and a heterocyclic quaternary salt.

The compound of the formula [I] of the present invention can be synthesized by, for example, the following method.

(i) when r=0

(a) $L^1$=$L^5$, X=Y, $R^1$=$R^2$ and $Z^1$=$Z^2$

A hetero ring quaternary salt compound (2 moles) of the formula [IV-1]

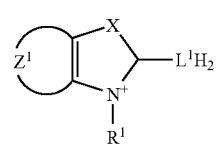

[IV-1]

wherein $L^1$, X, $Z^1$ and $R^1$ are as defined above, and a dianyl compound (1 mole) of the formula [V-1]

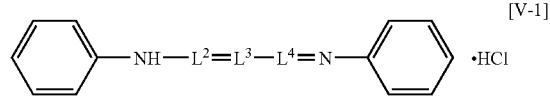

[V-1]

wherein $L^2$, $L^3$ and $L^4$ are as defined above, are reacted in the presence of a base and a solvent to give a compound of the formula [VI-1]

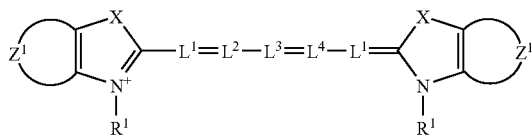

[VI-1]

wherein $L^1$, $L^2$, $L^3$, $L^4$, $R^1$, $Z^1$ and X are as defined above, and this compound [VI-1] (1 mole) and a necessary molar amount of the compound of the formula [VII]

$T^1$—Na    [VII]

wherein $T^1$ is an organic acid residue, are reacted to give a sodium salt of the compound of the above-mentioned formula [VI-1].

(b) $L^1 \neq L^5$ or $X \neq Y$ or $R^1 \neq R^2$ or $Z^1 \neq Z^2$

A hetero ring quaternary salt compound (1 mole) of the above-mentioned formula [IV-1] and the above-mentioned dianyl compound (1 mole) of the formula [V-1] are reacted in the presence of a base and a solvent to give a compound of the formula [VIII-1]

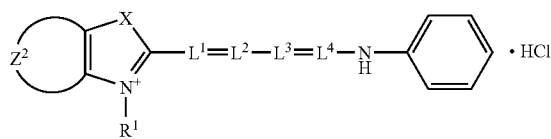

[VIII-1]

wherein $L^1$, $L^2$, $L^3$, $L^4$, $R^1$, $Z^1$ and X are as defined above, and this compound [VIII-1] (1 mole) and a hetero ring quaternary salt compound (1 mole) of the formula [XI-1]

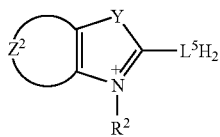

[XI-1]

wherein $L^5$, y, $Z^2$ and $R^2$ are as defined above, are reacted to give a compound of the formula [X-1]

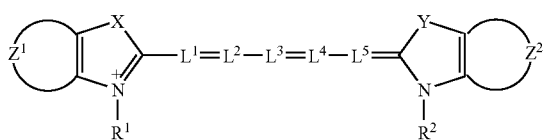

[X-1]

wherein $L^1$, $L^2$, $L^3$, $L^4$, $L^5$, $R^1$, $R^2$, $Z^1$, $Z^2$, X and Y are as defined above, and this compound of the formula [X-1] (1 mole) and a necessary molar amount of the above-mentioned compound of the formula [VII] are reacted to give a sodium salt of the compound of the above-mentioned formula [X-1].

(ii) when r=1

(a) $L^1 = L^7$, X=Y, $R^1 = R^2$ and $Z^1 = Z^2$

A hetero ring quaternary salt compound (2 moles) of the formula [IV-1]

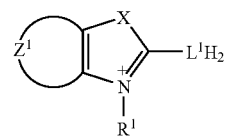

[IV-1]

wherein $L^1$, X, $Z^1$ and $R^1$ are as defined above, and a dianyl compound (1 mole) of the formula [V-2]

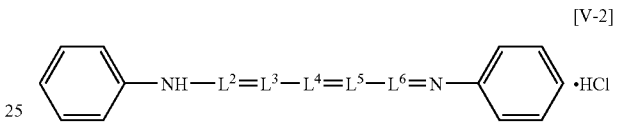

[V-2]

wherein $L^2$, $L^3$, $L^4$, $L^5$ and $L^6$ are as defined above, are reacted in the presence of a base and a solvent to give a compound of the formula [VI-2]

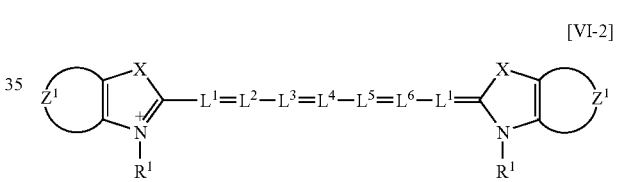

[VI-2]

wherein $L^1$, $L^2$, $L^3$, $L^4$, $L^5$, $L^6$, $R^1$, $Z^1$ and X are as defined above, and this compound [VI-2] (1 mole) and a necessary molar amount of the compound of the formula [VII]

$T^1$—Na    [VII]

wherein $T^1$ is as defined above, are reacted to give a sodium salt of the compound of the above-mentioned formula [VI-2].

(b) $L^1 \neq L^7$ or $X \neq Y$ or $R^1 \neq R^2$ or $Z^1 \neq Z^2$

A hetero ring quaternary salt compound (1 mole) of the above-mentioned formula [IV-1] and the above-mentioned dianyl compound (1 mole) of the formula [V-2] are reacted in the presence of a base and a solvent to give a compound of the formula [VIII-2]

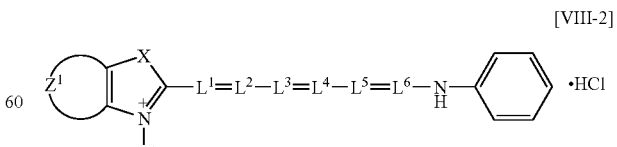

[VIII-2]

wherein $L^1$, $L^2$, $L^3$, $L^4$, $L^5$, $L^6$, $R^1$, $Z^1$ and X are as defined above, and this compound [VIII-2] (1 mole) and a hetero ring quaternary salt compound (1 mole) of the formula [IX-2]

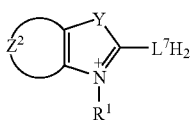

wherein $L^7$, y, $Z^2$ and $R^2$ are as defined above, are reacted to give a compound of the formula [X-2]

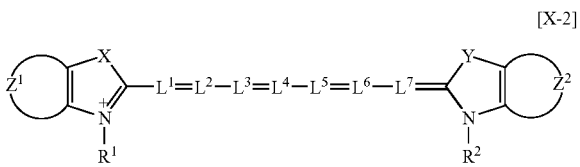

wherein $L^1, L^2, L^3, L^4, L^5, L^6, L^7, R^1, R^2, Z^1, Z^2, X$ and $Y$ are as defined above, and this compound of the formula [X-2] (1 mole) and a necessary molar amount of the above-mentioned compound of the formula [VII] are reacted to give a sodium salt of the compound of the above-mentioned formula [X-2].

(iii) when r=2

When r is 2, $L^6$ and $L^7$ overlap in the formula [I]. To avoid this, the overlapping $L^6$ and $L^7$ are referred to as $L^8$ and $L^9$ for clarification.

(a) $L^1=L^9$, X=Y, $R^1=R^2$ and $Z^1=Z^2$

A hetero ring quaternary salt compound (2 moles) of the formula [IV-1]

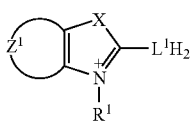

wherein $L^1$, X, $Z^1$ and $R^1$ are as defined above, and a dianyl compound (1 mole) of the formula [V-3]

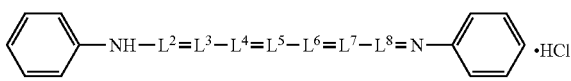

wherein $L^2, L^3, L^4, L^5, L^6$ and $L^7$ are as defined above and $L^8$ is an optionally substituted methine group, are reacted in the presence of a base and a solvent to give a compound of the formula [VI-3]

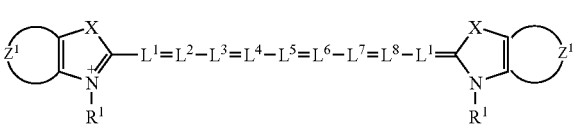

wherein $L^1, L^2, L^3, L^4, L^5, L^6, L^7, L^8, R^1, Z^1$ and X are as defined above, and this compound [VI-3] (1 mole) and a necessary molar amount of the compound of the formula [VII]

$$T^1-Na \qquad [VII]$$

wherein $T^1$ is as defined above, are reacted to give a sodium salt of the compound of the above-mentioned formula [VI-3].

(b) $L^1 \neq L^9$ or $X \neq Y$ or $R^1 \neq R^2$ or $Z^1 \neq Z^2$

A hetero ring quaternary salt compound (1 mole) of the above-mentioned formula [IV-1] and the above-mentioned dianyl compound (1 mole) of the formula [V-3] are reacted in the presence of a base and a solvent to give a compound of the formula [VIII-3]

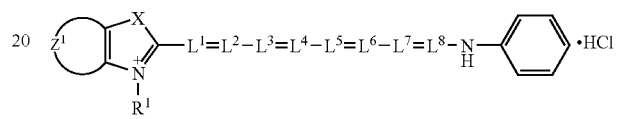

wherein $L^1, L^2, L^3, L^4, L^5, L^6, L^7, L^8, R^1, Z^1$ and X are as defined above, and this compound [VIII-3] (1 mole) and a hetero ring quaternary salt compound (1 mole) of the formula [IX-3]

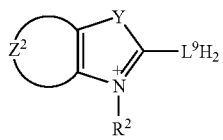

wherein Y, $Z^2$ and $R^2$ are as defined above and $L^9$ is an optionally substituted methine group, are reacted to give a compound of the formula [X-3]

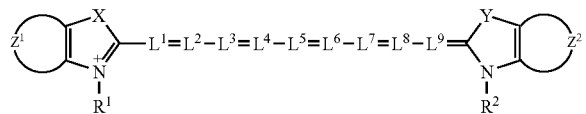

wherein $L^1, L^2, L^3, L^4, L^1, L^6, L^7, L^8, L^9, R^1, R^2, Z^1, Z^2$ X and Y are as defined above, and this compound of the formula [X-3] (1 mole) and a necessary molar amount of the above-mentioned compound of the formula [VII] are reacted to give a sodium salt of the compound of the above-mentioned formula [X-3].

The necessary molar amount of the compound of the formula [VII] is not less than the amount equivalent to the amount of sodium contained in one molecule of the objective sodium salt of the compound of the formula [I].

The substituent of the substituted methine group at $L^8$ and $L^9$ is exemplified by those mentioned with regard to the substituent of the above-mentioned methine groups at $L^1$ to $L^7$.

In the synthetic methods of the above-mentioned (i), (ii) and (iii), the reaction of the compounds [IV-1] and [V-1], that of the compounds [VIII-1] and [XI-1], that of the compounds

[IV-1] and [V-2], that of the compounds [VIII-2] and [IX-2], that of the compounds [IV-1] and [V-3] and that of the compounds [VIII-3] and [IX-3] proceed at a temperature of −20° C.-80° C., preferably −10° C.-40° C., preferably in the presence of an acylating agent such as acetic anhydride.

In the synthetic methods of the above-mentioned (i), (ii) and (iii), the reaction of the compounds [IV-1] and [VII], that of the compounds [X-1] and [VII], that of the compounds [VI-2] and [VII], that of the compounds [X-2] and [VII], that of the compounds [VI-3] and [VII] and that of the compounds [X-3] and [VII] proceed at a temperature of preferably 0° C.-40° C., preferably in the presence of a solvent such as alcohol and water.

In the synthetic methods of the above-mentioned (i), (ii) and (iii), the base to be used may be, for example, triethylamine, tributylamine, pyridine, diazabicycloundecene, sodium methoxide and the like; the solvent to be used may be, for example, an amide compound such as N,N-dimethylacetamide, N-methylpyrrolidone and N,N-diethylformamide or alcohols such as methanol; and the organic acid residue may be, for example, $CH_3COO$ and the like.

With regard to the production of various pharmaceutically acceptable salts of the compounds of the aforementioned formula [I], ammonium salt and potassium salt of the compounds of the formula [I] can be obtained by, for example, substituting the compound of the formula [VII] used in the above-mentioned synthetic methods (i), (ii) and (iii) with a compound of the formula [VII] wherein the sodium atom has been changed to ammonium group or potassium atom; and different cationic salts of the compounds of the aforementioned formula [I] can be obtained by converting said ammonium salt and potassium salt to different cationic salts by the use of ion exchange resins as necessary.

The compound of the above-mentioned formula [I] inclusive of the compound of the formula [II] to be used in the present invention are specifically exemplified in the following, to which the present invention is not limited.

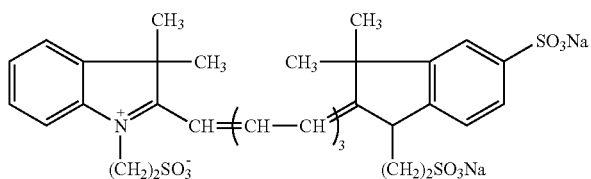

(1)

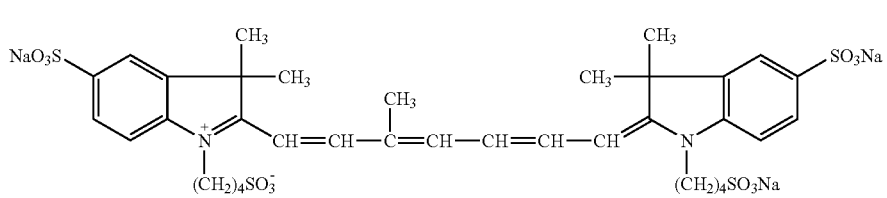

(2)

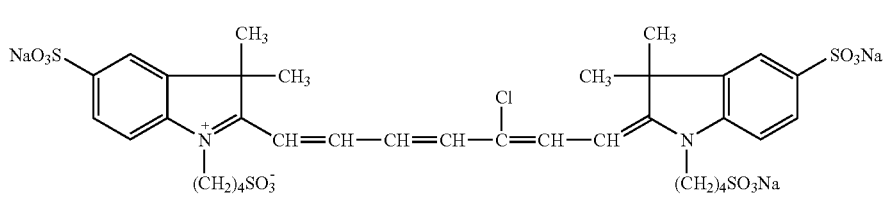

(3)

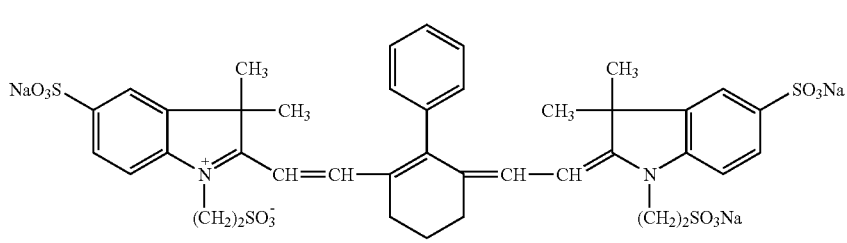

(4)

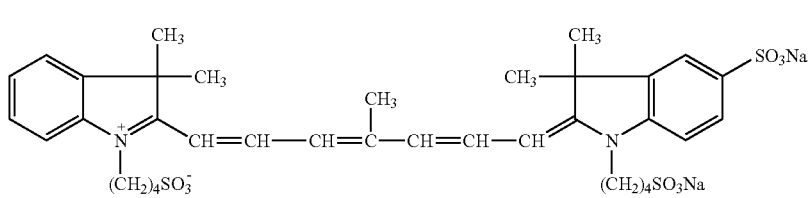

(5)

-continued
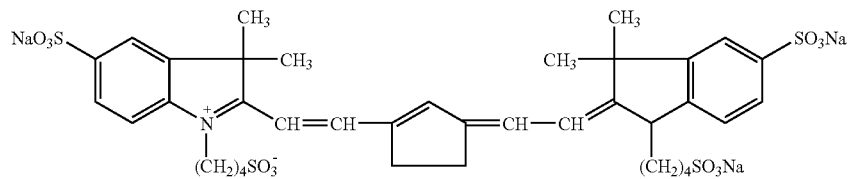
(6)
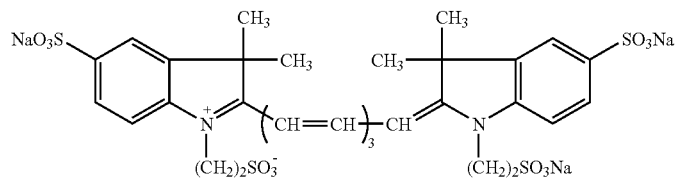
(7)
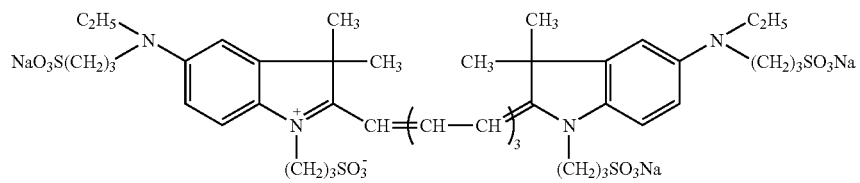
(8)
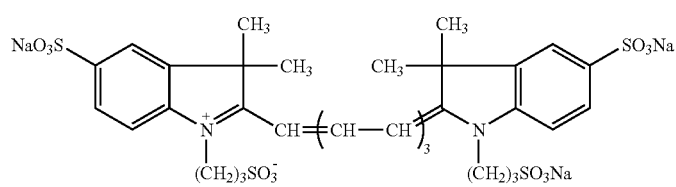
(9)
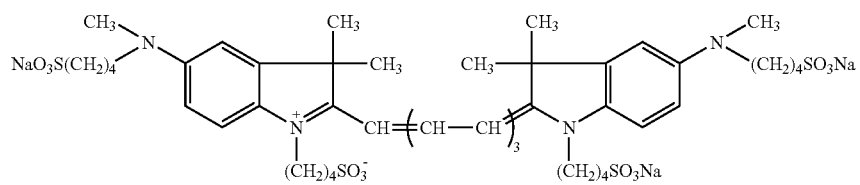
(10)
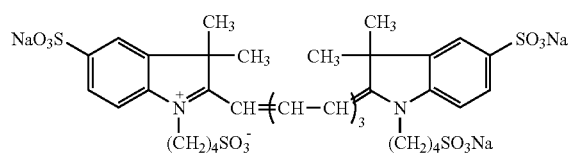
(11)
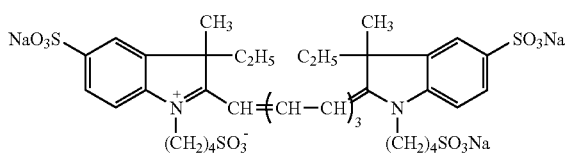
(12)
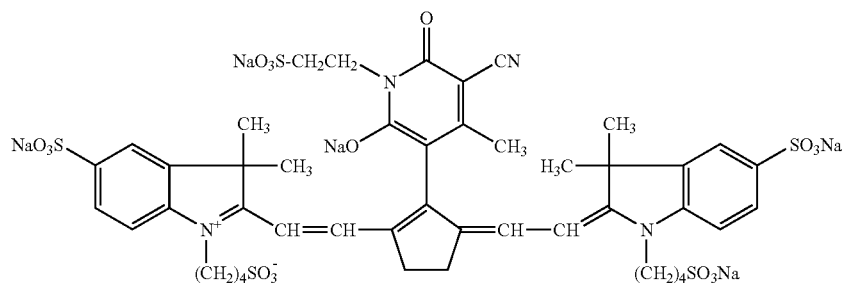
(13)
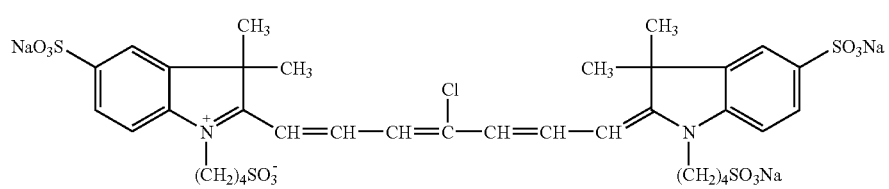
(14)

-continued
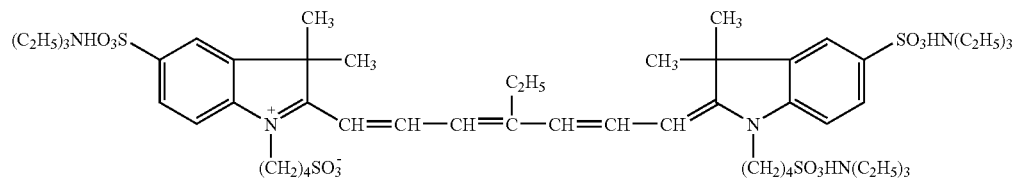
(15)
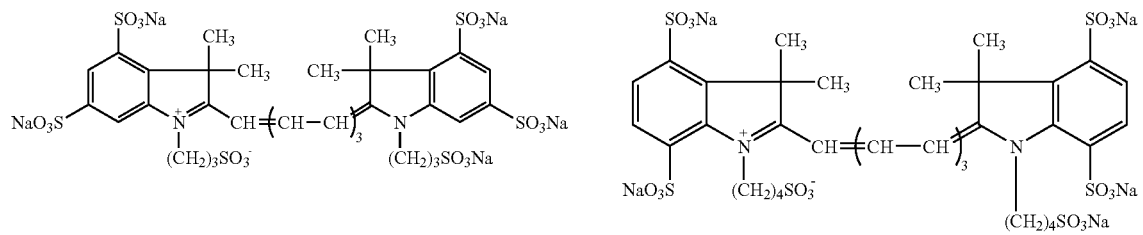
(16)
(17)
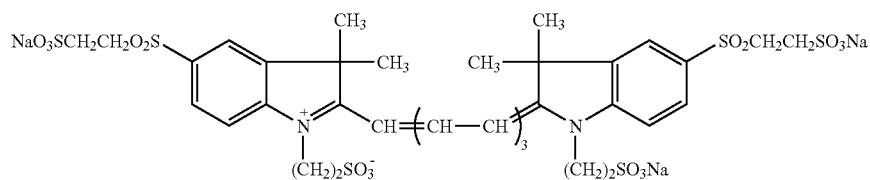
(18)
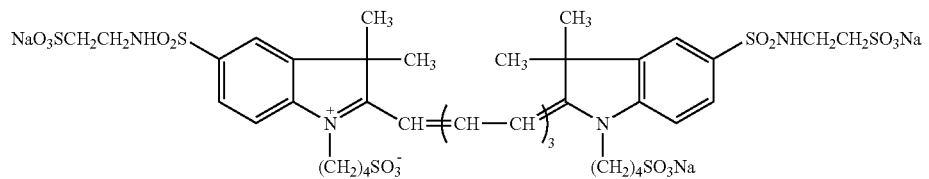
(19)
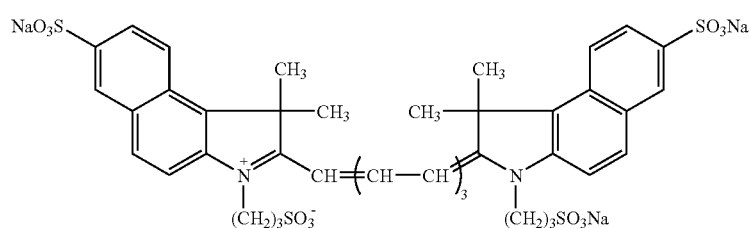
(20)
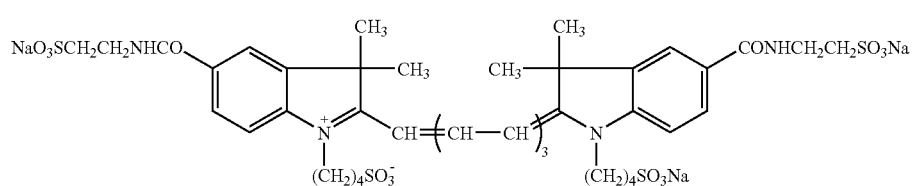
(21)
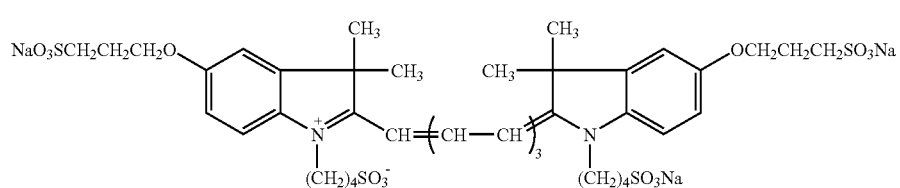
(22)

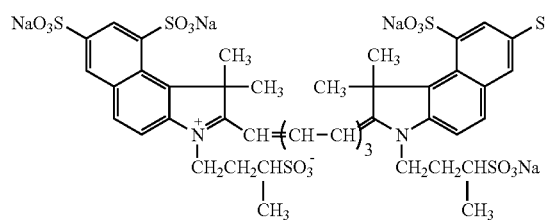 (23)
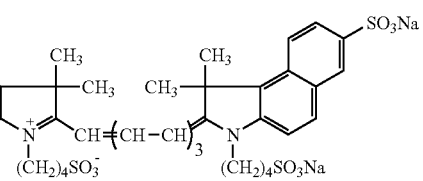 (24)
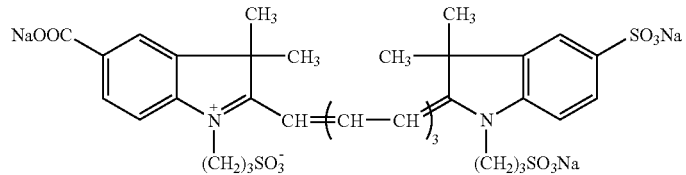 (25)
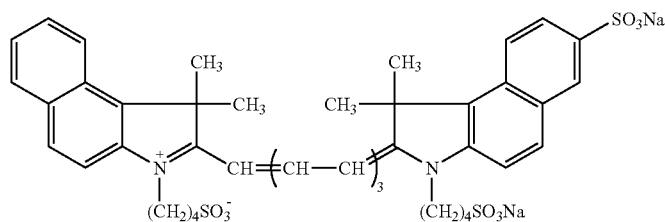 (26)
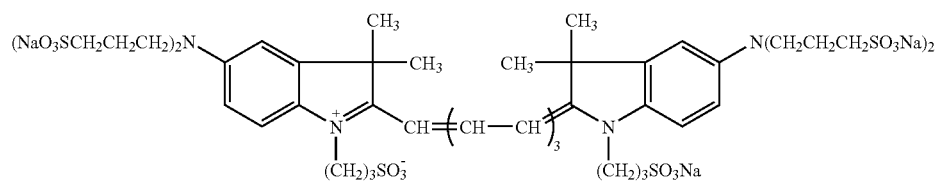 (27)
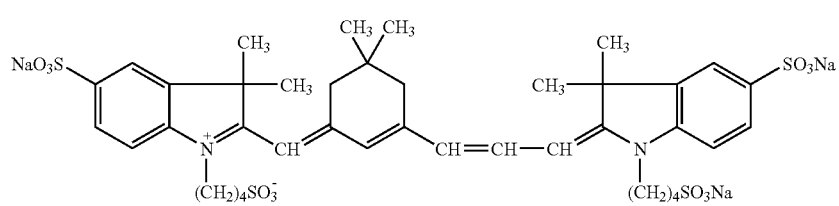 (28)
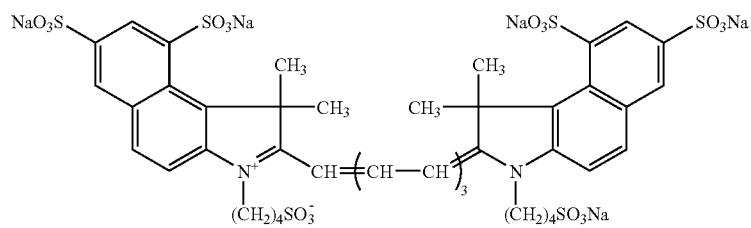 (29)
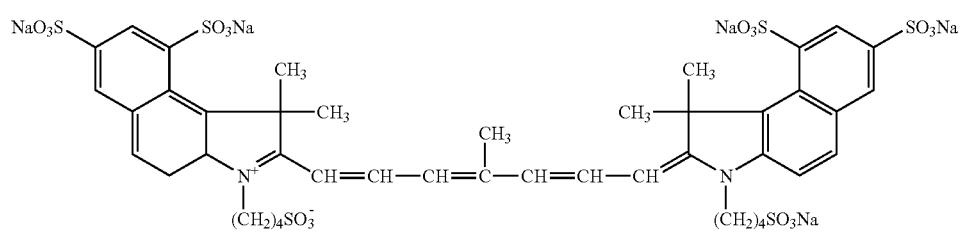 (30)

-continued
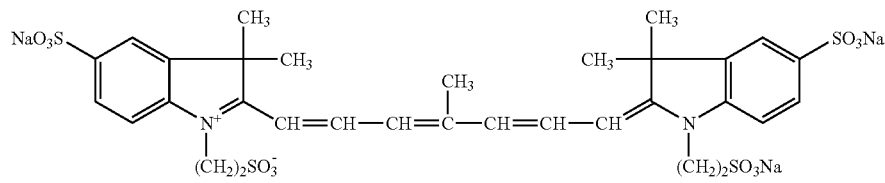
(31)
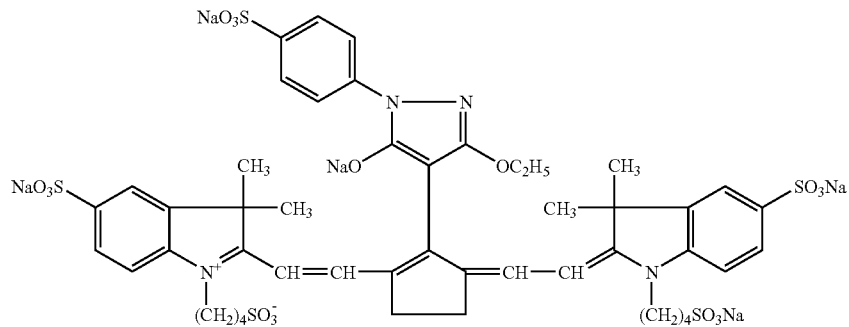
(32)
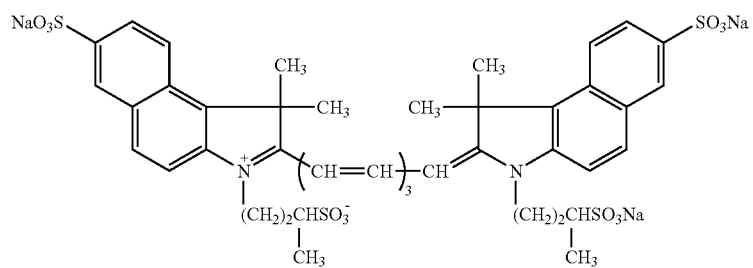
(33)
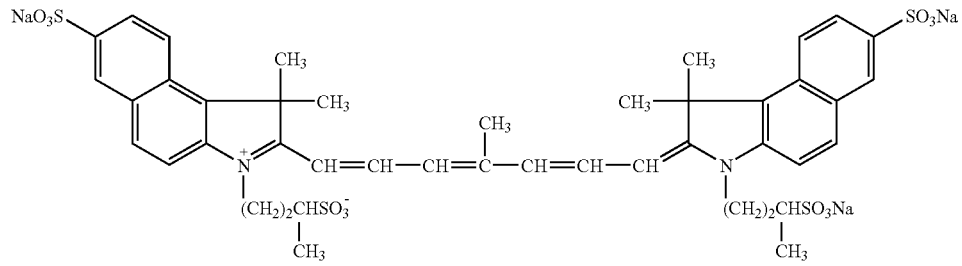
(34)
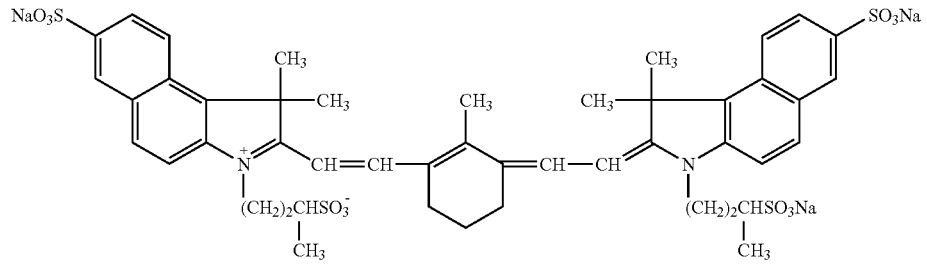
(35)
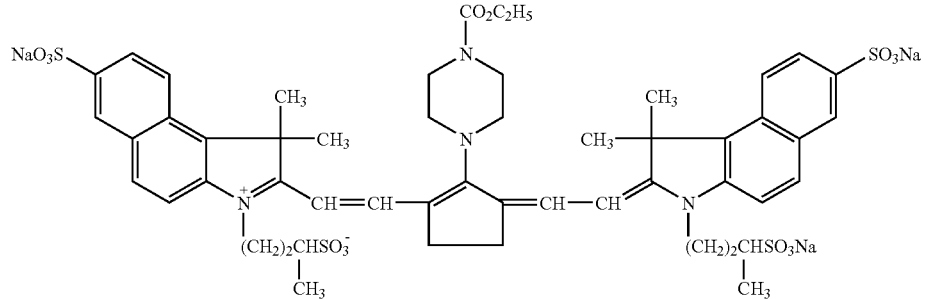
(36)

-continued
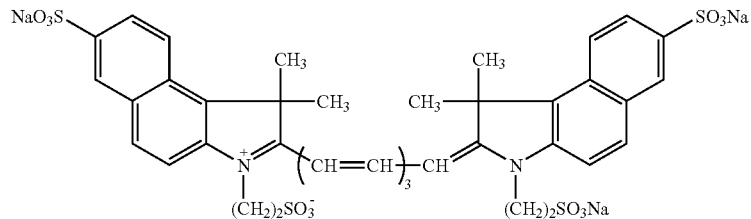 (37)
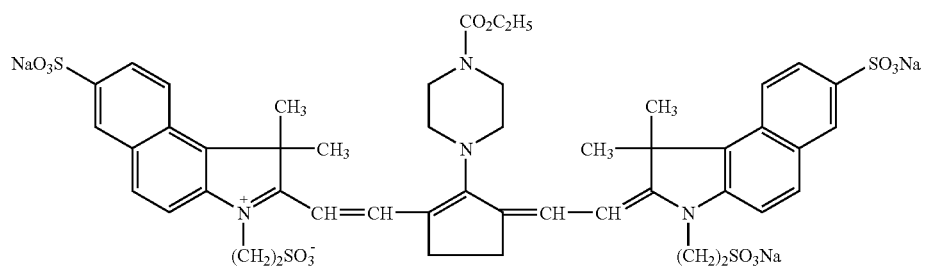 (38)
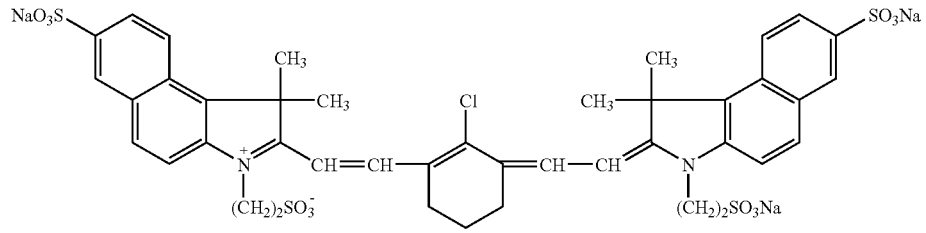 (39)
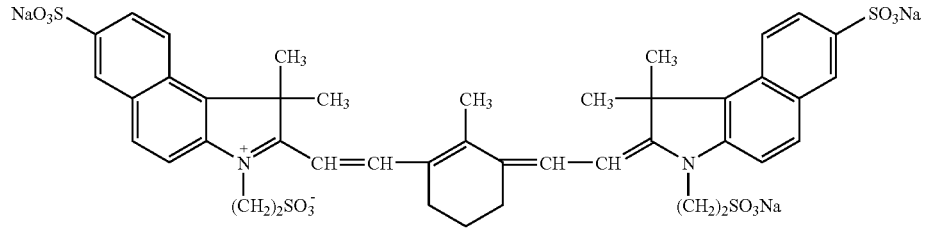 (40)
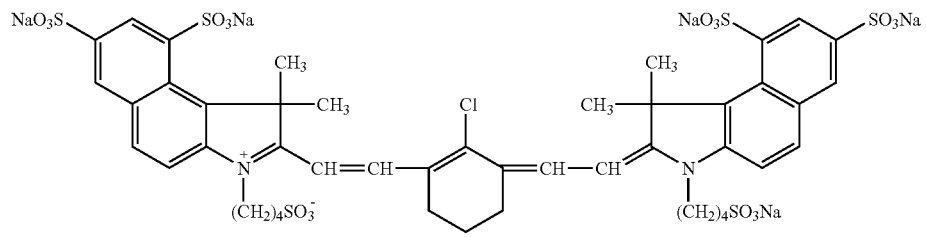 (41)
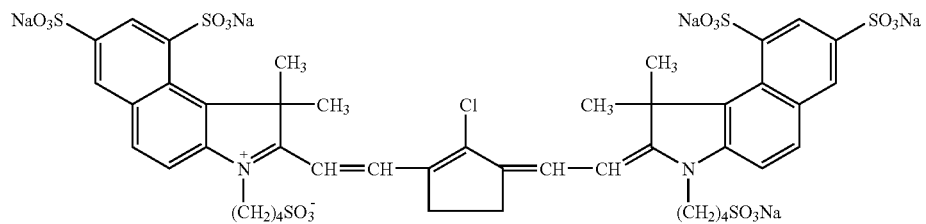 (42)
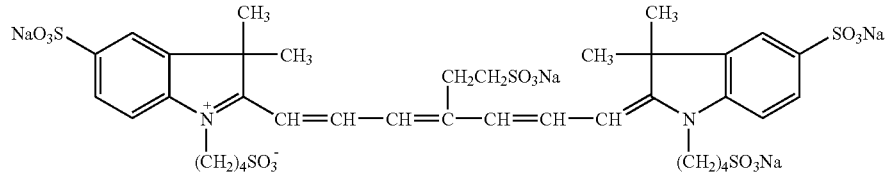 (43)

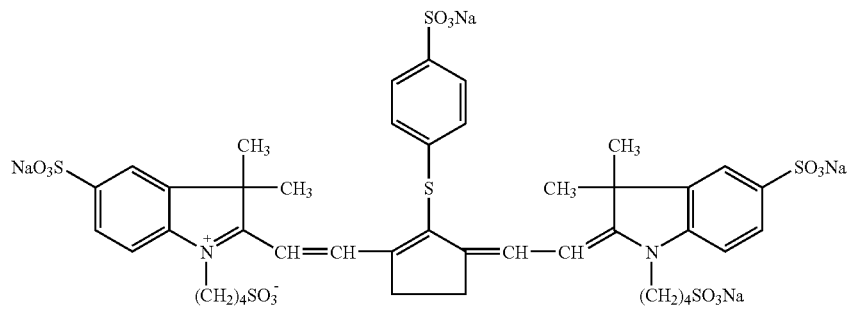
(44)
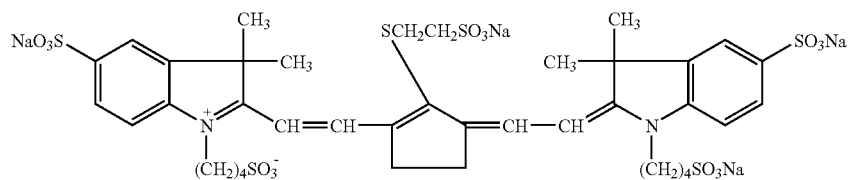
(45)
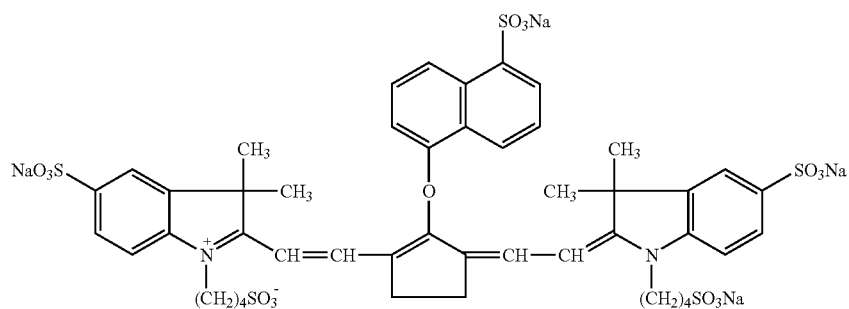
(46)
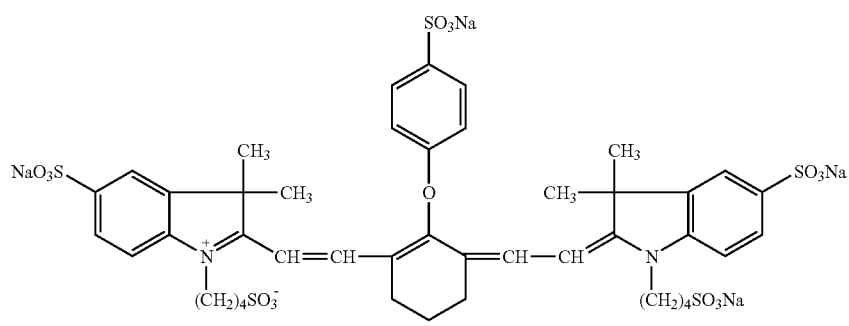
(47)
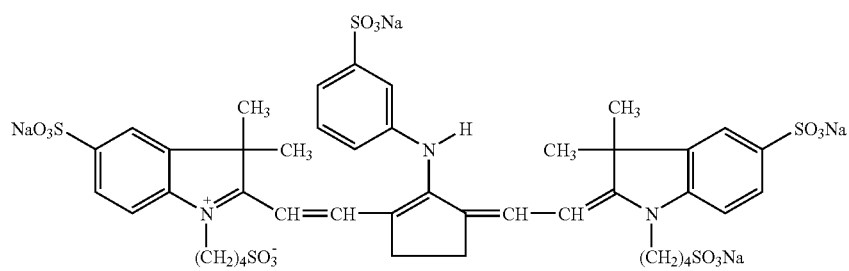
(48)

-continued
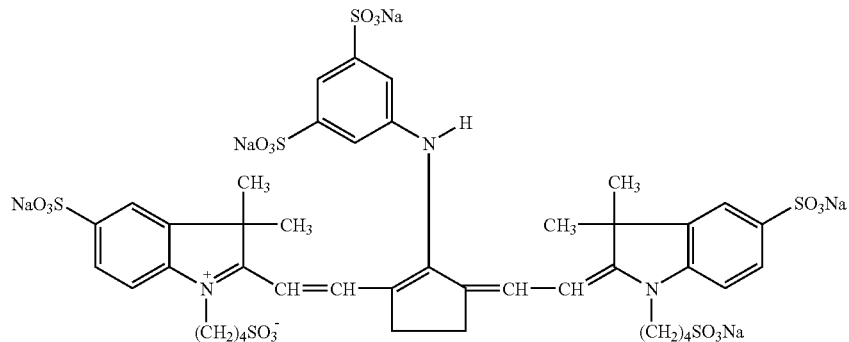
(49)
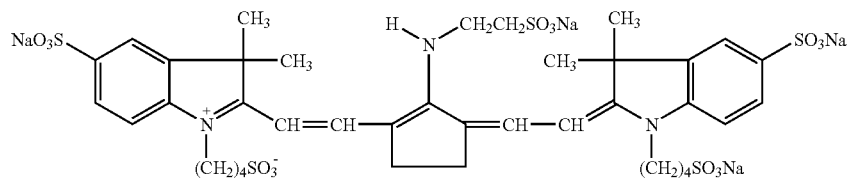
(50)
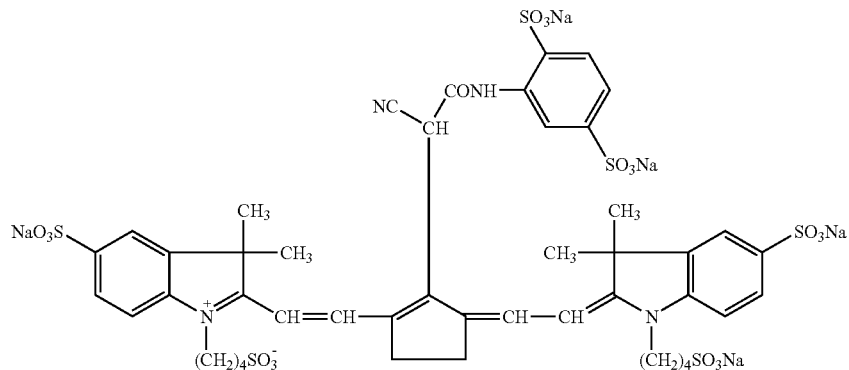
(51)
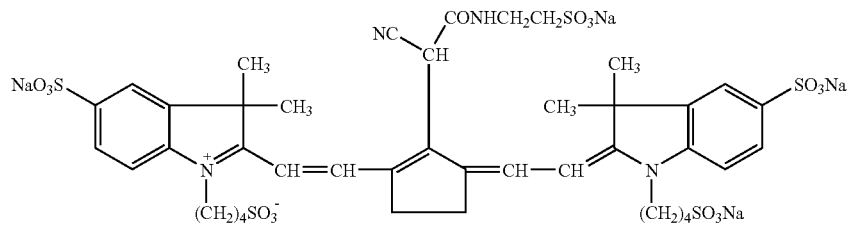
(52)
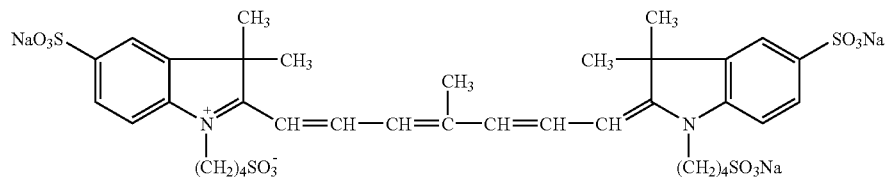
(53)
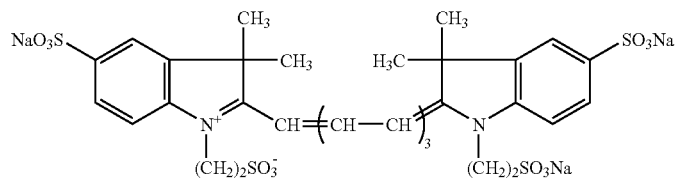
(54)

The above-mentioned compound to be contained in the near infrared fluorescent contrast agent of the present invention shows absorbance and fluorescence in the near infrared light region of 700-1300 nm, particularly about 700-900 nm, and has a molar absorption coefficient of not less than 100,000.

The near infrared fluorescent contrast agent of the present invention is subject to no particular limitation as long as it contains a compound of the formula [I] or formula [II] and/or a pharmaceutically acceptable salt thereof, and has 3 or more, preferably 4 or more, sulfonic acid groups in a molecule. This compound or a salt thereof alone or in combination may be contained in said contrast agent.

To be specific, said contrast agent includes said compound or said compound suspended or dissolved in a solvent, such as injectable distilled water, physiological saline, Ringer solution and the like. Where necessary, pharmacologically acceptable additives such as carrier, excipient and the like may be added. These additives contain substances such as pharmacologically acceptable electrolyte, buffer, detergent and a substance for adjusting osmotic pressure and improving stability and solubility (e.g., cyclodextrin, liposome and the like). Various additives generally used in the pertinent fields may be used. The near infrared fluorescent contrast agent of the present invention is preferably produced through a sterilization process when it is intended for pharmaceutical use.

Said contrast agent can be administered to a living body by injecting, spraying or coating, intravascularly (venous, arterial), orally, intraperitoneally, percutaneously, subcutaneously, intracystically or intrabronchially. Preferably, the agent is administered into blood vessels in the form of an aqueous agent, emulsion or suspension.

The dose of the near infrared fluorescent contrast agent of the present invention is not particularly limited insofar as the dose enables detection of the site to be ultimately diagnosed. It is appropriately adjusted depending on the kind of compound to be used that emits near infrared fluorescence, age, body weight and target organ of administration subjects, and the like. Typically, the dose is 0.1-100 mg/kg body weight, preferably 0.5-20 mg/kg body weight, in the amount of said compound.

The contrast agent of the present invention can be appropriately used for various animals other than human. The administration form, route and dose are suitably determined depending on the body weight and conditions of the target animals.

In the present invention, moreover, the above-mentioned compound of the formula [I], particularly preferably [II], having 3 or more, preferably 4 or more, sulfonic acid groups in a molecule tends to be noticeably accumulated in tumor tissues. Utilizing this characteristic, a tumor tissue can be specifically imaged using the inventive fluorescent contrast agent. In addition, a series of said compounds can reside in blood vessel for a long time and they are expected to serve well as angiography contrast agents.

The fluorescence imaging method of the present invention is characterized by the use of the inventive near infrared fluorescent contrast agent. This method is practiced following known methods, and each parameter, such as excitation wavelength and fluorescence wavelength to be detected, is appropriately determined to achieve optimal imaging and evaluation, depending on the kind of near infrared fluorescent contrast agent to be administered and administration targets. The time spent from administration of the inventive near infrared fluorescent contrast agent to determination target to the initiation of determination by the inventive fluorescence imaging method varies depending on the kind of the near infrared fluorescent contrast agent to be used and administration targets. For example, when the agent contains a compound of the formula [I] for tumor imaging, the lapse time will be about 4-120 hours after administration. In the case of compound of formula [II], the lapse time will be about 24-120 hours after administration. When the lapse time is too short, the fluorescence is so intense that the target site and other site cannot be clearly divided. When it is too long, said contrast agent may be cleared from the body. When imaging of blood vessel is desired, the compound of the formula [I] or formula [II] is detected immediately after administration or in about 30 minutes thereafter.

The method typically includes the following steps.

That is, a near infrared fluorescent contrast agent of the present invention is administered to a detection target and the detection target is exposed to an excitation light from an excitation light source. Then, fluorescence from the near infrared fluorescent contrast agent, which has been caused by said excitation light, is detected with a fluorescence detector.

The wavelength for excitation varies depending on the near infrared fluorescent contrast agent to be used. It is free of limitation as long as said compound efficiently emits fluorescence in the near infrared region. Preferably, a near infrared light having superior biotransmission capability is used.

The wavelength of the near infrared fluorescence to be detected also varies depending on the contrast agent to be used. In general terms, an excitation light having a wavelength of 600-1000 nm, preferably 700-850 nm, is used and near infrared fluorescence in a region at a wavelength of 700-1000 nm, preferably 750-900 nm, is detected. In this case, the excitation light source may be a conventional excitation light source, such as various lasers (e.g., ion laser, dye laser and semiconductor laser), halogen light source, xenon light source and the like. Where necessary, various optical filters may be used to obtain optimal excitation wavelength. Likewise, fluorescence may be detected using various optical filters to pick up only fluorescence from said near infrared fluorescent contrast agent.

The detected fluorescence is data-processed as fluorescence information and used to generate fluorescence images that can be recorded. The fluorescence images are generated by irradiating a wide area including the target tissue, detecting fluorescence with a CCD camera and image-processing the obtained fluorescence information. Alternatively, an optical CT device may be used, an endoscope may be used, or a fundus camera may be used.

The fluorescence imaging method of the present invention enables visualizing systemic diseases, tumors, blood vessels and the like without damaging a living body.

The present invention is explained in more detail by way of Examples and Experimental Examples, to which the present invention is not limited. The compound numbers in the following Examples and Experimental Examples correspond to those of the compounds explained by structural formulas.

The compound wherein a symbol designating "potassium salt", "calcium salt" or "pyridinium salt" is indicated after the compound number (e.g. compound (29) K salt) means a compound that is the same as the compound expressed by the compound number (sodium salt) except that the counter ion is potassium salt, calcium salt or pyridinium salt instead of sodium salt. For example, "compound (31) K salt" means a compound that is the same as the compound (31) except that the counter ion is potassium instead of sodium; "compound (31) Ca salt" means a compound that is the same as compound (31) except that the counter ion is calcium instead of sodium; and "compound (31) pyridinium" salt means a compound that is the same as compound (31) except that the counter ion is pyridinium instead of sodium.

The synthetic method of the compound to be contained in the near infrared fluorescent contrast agent of the present invention as an active ingredient is explained in Examples.

The following synthetic methods mostly consist of reactions of heterocyclic quaternary salt compound shown in Table 1 and dianyl compounds shown in Tables 2 and 3.

TABLE 1

Heterocyclic quaternary salt compound

| Symbol | Structural formula [Registration No. in Chemical Abstract (CA)] | Source/Synthetic method |
|---|---|---|
| Q1 | 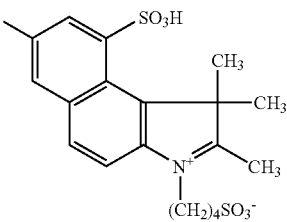<br>(138913-76-5) | In the same manner as Q2, corresponding indolenin derivative is reacted with butanesulton. |
| Q2 | 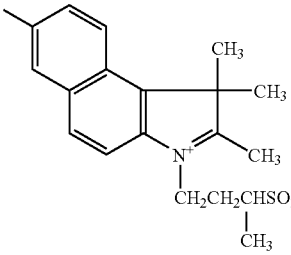<br>(113995-56-5) | JP-A 63-55544<br>EP 251282 |
| Q3 | 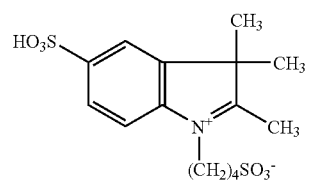<br>(76588-81-3) | JP-A 2-233658<br>CA 114:122053 |
| Q4 | 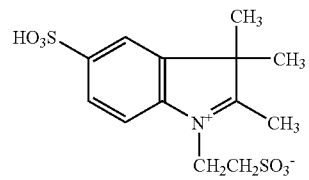<br>(183272-36-8) | In the same manner as Q3, corresponding indolenin derivative is reacted with 2-bromoethanesulfonic acid. |

TABLE 2

Dianyl compound-1

| Symbol | Structural formula [Registration No. in Chemical Abstract (CA)] | Source/Synthetic method |
|---|---|---|
| A1 | 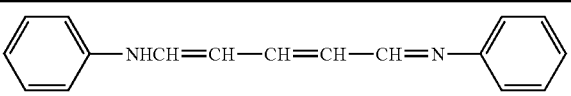 (1497-49-0) ·HCl | Reagent commercially available from Aldrich and others |
| A2 | 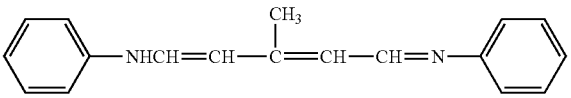 (1979-58-4) ·HCl | JP-A 8-295658 CA 126:90721 |
| A3 | 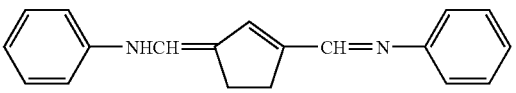 (53019-66-2) ·HCl | Zh.Org.Khim., 13(6) 1189-92 (1977) CA 87:102034 |
| A4 | 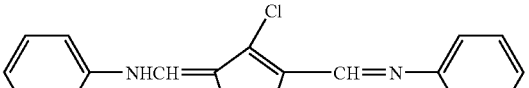 (63856-99-5) ·HCl | Zh.Org.Khim., 13(6) 1189-92 (1977) CA 87:102034 |

TABLE 3

Dianyl compound-2

| Symbol | Structural formula [Registration No. in Chemical Abstract (CA)] | Source/Synthetic method |
|---|---|---|
| A5 | 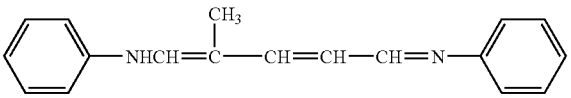 (77146-76-0) ·HCl | Nukleofil' nye Reacts. Karbonil' nykn Soedin (1982), 52-53 CA 101:130179 |
| A6 | 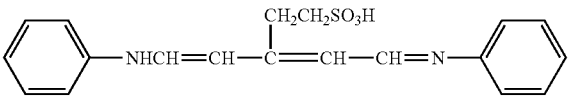 (125577-71-1) ·HCl | Ger Offem, DE 2928184 CA 94:176696 |
| A7 | 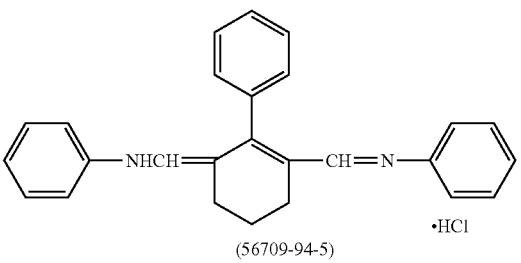 (56709-94-5) ·HCl | Zh.Org.Khim., 18(10) 2176-9 (1982) CA 98:73808 |
| A8 | 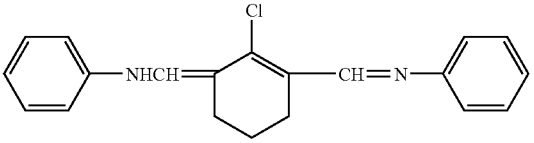 (63857-00-1) HCl | Zh.Org.Khim., 13(6) 1189-92 (1977) CA 87:102034 |

EXAMPLES

In the following Examples, the compounds are referred to with the symbols (e.g., A1, Q1 and the like) used in Tables 1 to 3 for the convenience's sake.

Example 1

Synthesis of Compound (29)

To heterocyclic quaternary salt compound Q1 (5 g) were added methanol (100 ml), N,N-dimethylformamide (25 ml), triethylamine (5.6 ml), dianyl compound A1 (1.83 g) and acetic anhydride (3 ml), and the mixture was stirred at room temperature for 4 hours. Triethyl amine (2.2 ml) and acetic anhydride (2 ml) were added, and the mixture was stirred at room temperature for 3 hours. The insoluble matter was filtered off, and a solution of sodium acetate (2 g) in methanol (15 ml) was added to the filtrate, which was followed by stirring at room temperature for 1 hour. The resulting crystals were collected by filtration and washed with a small amount of methanol. To the obtained crude crystals (3.5 g) was added water (20 ml) for dissolution. Sodium acetate (1 g) was added, and then methanol (30 ml) was added, which was followed by stirring for 1 hour. The resulting crystals were collected by filtration, washed with a small amount of methanol and dried to give 3 g of compound (29). The obtained compound (29) showed yellow in a flame test.

Maximum wavelength of absorbance ($H_2O$): 780 nm

Molar absorption coefficient ($H_2O$): 0.243,000

Maximum wavelength of fluorescence emission ($H_2O$): 802 nm

Figure 11:
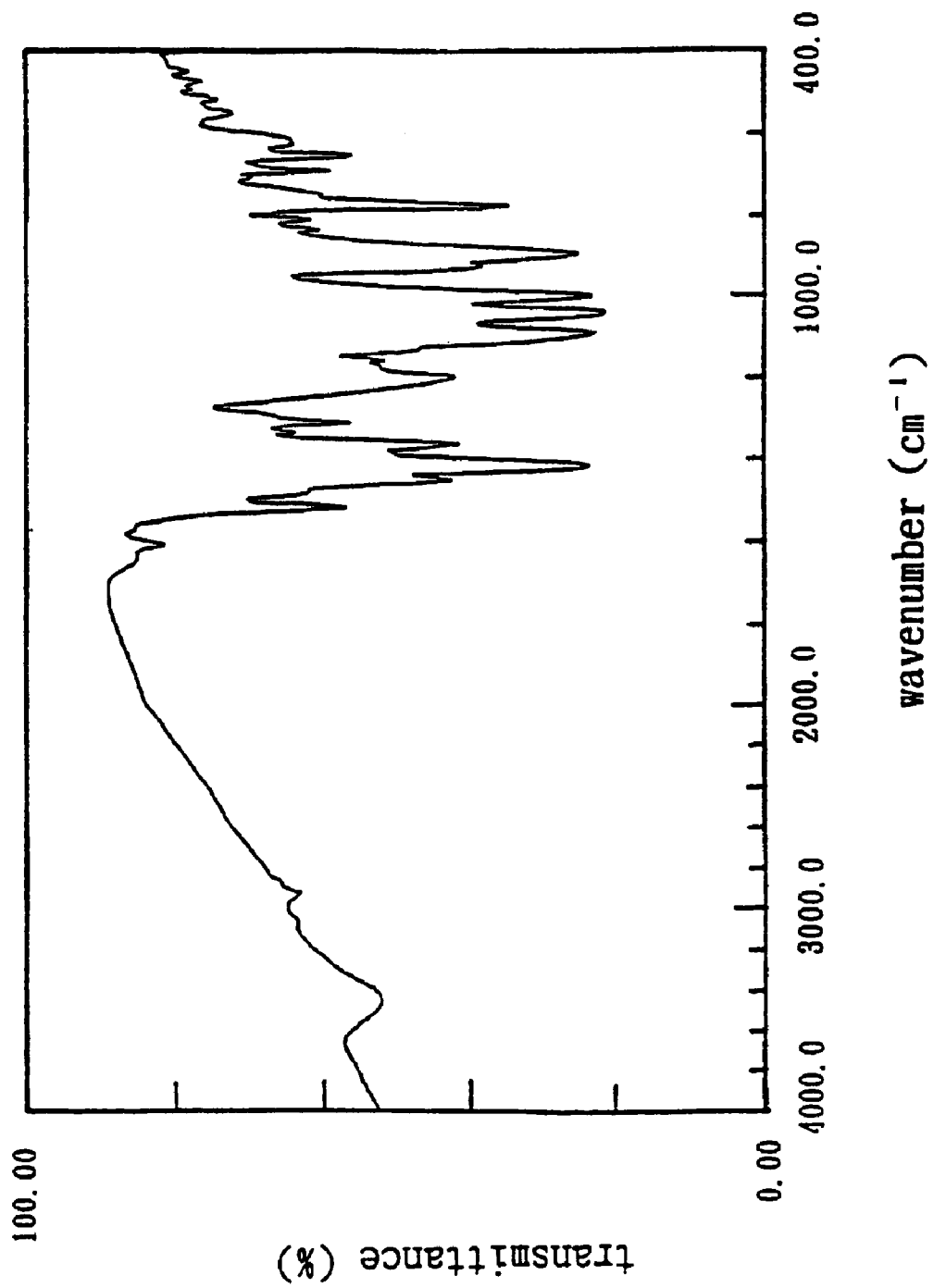
FIG. 11 is a chart showing the infrared absorption spectrum of compound (29).

The infrared absorption spectrum was measured for the obtained compound (29) by potassium bromide tablet method using a Fourier transform infrared spectrometer (VALOR-III, manufactured by JASCO). The following peaks were detected. The spectrum is shown in FIG. 11.

IR ($\square$max(KBr)): 1414, 1086, 1037, 995, 889 $cm^{-1}$

Example 2

Synthesis of Compound (34)

To heterocyclic quaternary salt compound Q2 (2.13 g) was added methanol (20 ml) and the mixture was cooled to 10° C. Thereto were added dianyl compound A2 (0.75 g), triethylamine (4 ml) and acetic anhydride (2 ml), and the mixture was stirred for 20 minutes. Acetic anhydride (2 ml) was added, and the mixture was stirred at 10° C. for 4 hours. The insoluble matter was filtered off, and a solution of sodium acetate (2 g) in a small amount of methanol was added to the filtrate. The resulting crystals were collected by filtration and washed with a small amount of methanol. To the obtained crude crystals was added water (7 ml) for dissolution. Methanol (7 ml) was added to precipitate crystals. The resulting crystals were collected by filtration, washed with a small amount of methanol and dried to give 1.2 g of compound (34). The obtained compound (34) showed yellow in a flame test.

Maximum wavelength of absorbance ($H_2O$): 794 nm

Molar absorption coefficient ($H_2O$): 176,000

Maximum wavelength of fluorescence emission ($H_2O$): 812 nm

Example 3

Synthesis of Compound (6)

To heterocyclic quaternary salt compound Q3 (9.5 g) are added methanol (50 ml), triethylamine (7 ml), dianyl compound A3 (3.1 g) and acetic anhydride (3.9 ml), and the mixture is stirred at room temperature for 7 hours. The insoluble matter is filtered off, and a solution of sodium acetate (5 g) in a small amount of methanol is added to the filtrate. The mixture is stood overnight. The resulting crystals are collected by filtration and washed with a small amount of methanol. To the crystals is added water (30 ml) for dissolution. Sodium acetate (2 g) is added, and then methanol (30 ml) is added. The resulting crystals are collected by filtration, washed with a small amount of methanol and dried to give compound (6).

Example 4

Synthesis of Compound (45)

To heterocyclic quaternary salt compound Q3 (4.8 g) were added methanol (50 ml), triethylamine (4 ml), dianyl compound A4 (1.7 g) and acetic anhydride (2 ml), and the mixture was stirred at room temperature for 3 hours. The insoluble matter was filtered off, and a solution of sodium acetate (4 g) in a small amount of methanol was added to the filtrate. The resulting crystals were collected by filtration and washed with a small amount of methanol. To the crystals was added water (10 ml) for dissolution. Then methanol (10 ml) was added. The resulting crystals were collected by filtration, washed with a small amount of methanol and air dried to give 1.6 g of a compound that is the same as compound (45) except that the substituent on the methine chain is —Cl instead of —$SCH_2CH_2SO_3Na$.

The above step was repeated to give 4.2 g of said compound. Thereto were added water (30 ml), triethylamine (1.2 ml) and sodium 2-mercaptoethanesulfonate (0.8 g), and the mixture was stirred at room temperature for 4 hours. The insoluble matter was filtered off, and a solution of sodium acetate (2 g) in a small amount of water was added to the filtrate. The resulting crystals were collected by filtration, washed with methanol (20 ml) and air dried to give 2.3 g of compound (45). The obtained compound (45) showed yellow in a flame test.

Maximum wavelength of absorbance ($H_2O$): 815 nm

Molar absorption coefficient ($H_2O$): 196,000

Maximum wavelength of fluorescence emission ($H_2O$): 827 nm

Example 5

Synthesis of Compound (2)

To heterocyclic quaternary salt compound Q3 (4.7 g) are added methanol (25 ml), triethylamine (2.8 ml), dianyl compound A5 (1.5 g) and acetic anhydride (2.4 ml), and the mixture is stirred at room temperature for 1 hour. Thereto are further added triethyl amine (3.5 ml) and acetic anhydride (1.5 ml), and the mixture is stirred at room temperature for 3.5 hours. The insoluble matter is filtered off, and a solution of sodium acetate (3 g) in a small amount of methanol is added to the filtrate. The mixture is stirred at room temperature for 1 hour. The resulting crystals are collected by filtration and washed with a small amount of methanol. To the crystals is added water (15 ml) for dissolution. Then methanol (15 ml) is added. The resulting crystals are collected by filtration, washed with a small amount of methanol and dried to give compound (2).

Example 6

Synthesis of Compound (43)

To heterocyclic quaternary salt compound Q3 (3.75 g) were added methanol (25 ml), triethylamine (3.5 ml), dianyl compound A6 (1.95 g) and acetic anhydride (2.4 ml), and the mixture was stirred at room temperature for 1 hour. The insoluble matter was filtered off, and a solution of sodium acetate (3.9 g) in a small amount of methanol was added to the filtrate. The mixture was stirred at room temperature for 1 hour. The resulting crystals were collected by filtration and washed with a small amount of methanol. To the crystals was added water (10 ml) for dissolution. Sodium acetate (2 g) was added, and then methanol (10 ml) was added. The resulting crystals were collected by filtration, washed with a small amount of methanol and dried to give 1.8 g of compound (43). The obtained compound (43) showed yellow in a flame test.

Maximum wavelength of absorbance ($H_2O$): 773 nm
Molar absorption coefficient ($H_2O$): 204,000
Maximum wavelength of fluorescence emission ($H_2O$): 789 nm

Example 7

Synthesis of Compound (4)

To heterocyclic quaternary salt compound Q3 (3.5 g) are added methanol (20 ml), triethylamine (3.5 ml), dianyl compound A7 (1.2 g) and acetic anhydride (1.9 ml), and the mixture is stirred at room temperature for 10 hours, and then stood overnight. The mixture is stirred under heating at 50° C. for 5 hours. Water (2 ml) is added and the insoluble matter is filtered off. A solution of sodium acetate (5 g) in a small amount of water is added to the filtrate. The mixture is stirred at room temperature for 30 minutes. The resulting crystals are collected by filtration and washed with a small amount of methanol and dried to give compound (4).

Example 8

Synthesis of Compound (31)

To heterocyclic quaternary salt compound Q4 (3.5 g) were added methanol (35 ml), triethylamine (3.5 ml) and acetic anhydride (2 ml), and dianyl compound A2 (1.8 g) was added portionwise with stirring. The mixture was further stirred for 1 hour. Acetic anhydride (2 ml) was added, and the mixture was stirred at room temperature for 5 hours. The insoluble matter was filtered off, and a solution of sodium acetate (4 g) in a small amount of methanol was added to the filtrate. The resulting crystals were collected by filtration and washed with a small amount of methanol. To the crystals was added water (10 ml) for dissolution. Then methanol (10 ml) was added, and the mixture was stirred at room temperature for 2 hours. The resulting crystals were collected by filtration, washed with a small amount of methanol and dried to give 1.3 g of compound (31). The obtained compound (31) showed yellow in a flame test.

Figure 12:
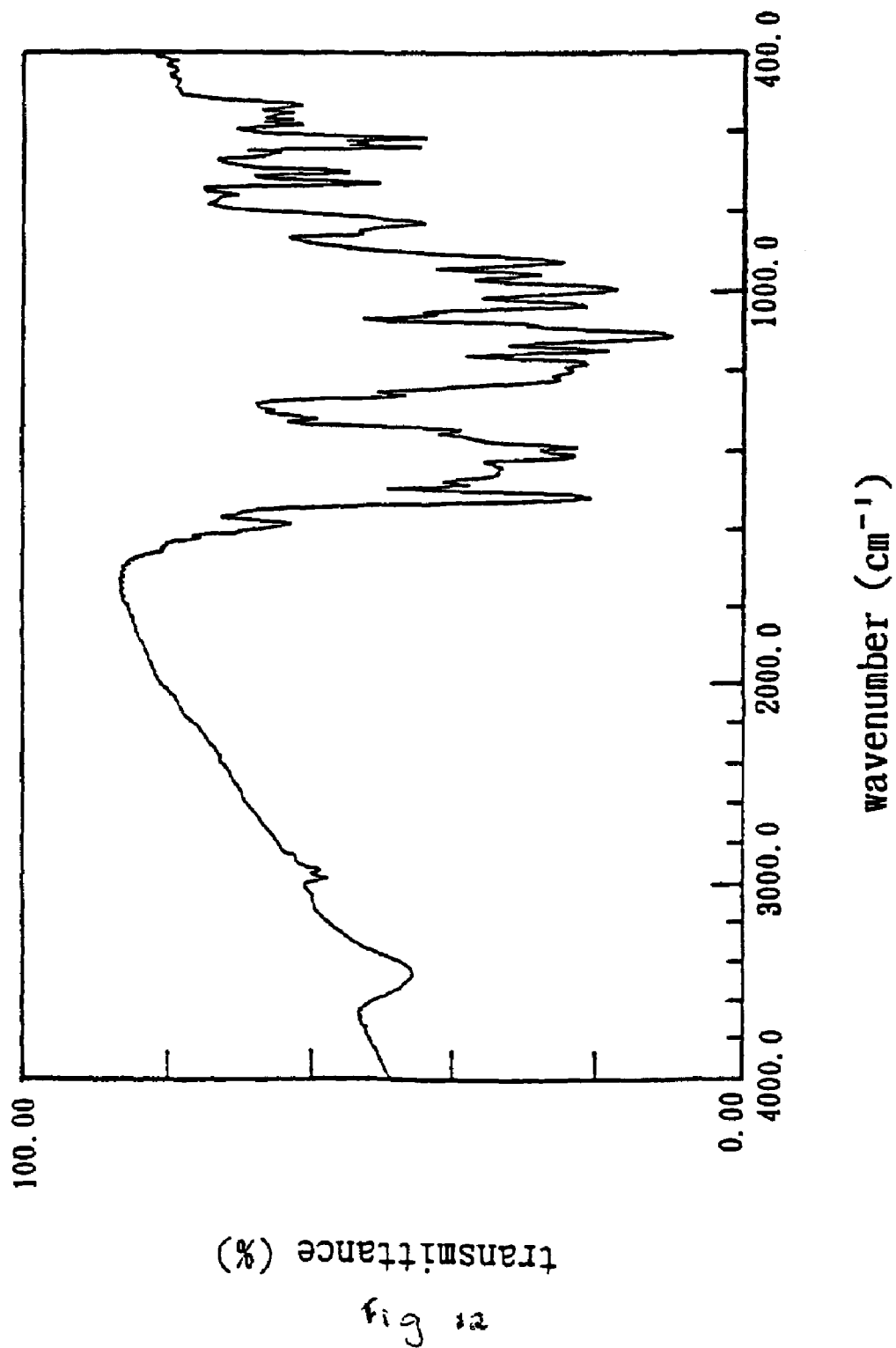
FIG. 12 is a chart showing the infrared absorption spectrum of compound (31).

Maximum wavelength of absorbance ($H_2O$): 755 nm
Molar absorption coefficient ($H_2O$): 228,000
Maximum wavelength of fluorescence emission ($H_2O$): 774 nm The infrared absorption spectrum was measured for the obtained compound (31) by potassium bromide tablet method using a Fourier transform infrared spectrometer (VALOR-III, manufactured by JASCO). The following peaks were detected. The spectrum is shown in FIG. 12.

IR (vmax(KBr)): 1518, 1183, 1149, 1111, 995 $cm^{-1}$

Example 9

Synthesis of Compound (41)

To heterocyclic quaternary salt compound Q1 (12 g) were added methanol (120 ml), triethylamine (13.6 ml), dianyl compound A8 (4.4 g) and acetic anhydride (2.4 ml), and the mixture was stirred for 30 minutes. Acetic anhydride (2.4 ml) was added and the mixture was stirred for 1.5 hours, and then acetic anhydride (2.4 ml) was added and the mixture was stirred at room temperature for 6 hours. Heterocyclic quaternary salt compound Q1 (1 g), triethyl amine (3 ml) and acetic anhydride (3 ml) were further added and the mixture was stirred at room temperature for 2 hours. The mixture was stood overnight. Sodium acetate (5 g) was added and the resulting crystals were collected by filtration and washed with a small amount of methanol. To the obtained crude crystals was added water (200 ml). The insoluble matter was filtered off, and sodium acetate (10 g) was added to the filtrate. The resulting crystals were collected by filtration and washed with a small amount of methanol. To the crystals were added water (200 ml) and triethylamine (10 ml), and a solution of sodium acetate (10 g) in methanol (100 ml) was added to give crystals. This step was repeated twice. The resulting crystals were collected by filtration, washed with a small amount of methanol and dried to give 9.7 g of compound (41). The obtained compound (41) showed yellow in a flame test.

Maximum wavelength of absorbance ($H_2O$): 811 nm
Molar absorption coefficient ($H_2O$): 230,000
Maximum wavelength of fluorescence emission ($H_2O$): 822 nm

Example 10

Synthesis of Compound (3)

According to Example 5, heterocyclic quaternary salt compound Q3 and the corresponding dianyl compound are used to give compound (3).

Example 11

In the same manner as in the synthesis of compound (29) in Example 1 except that potassium acetate (2 g) was used instead of sodium acetate (2 g), a compound that is the same as compound (29) except that the counter ion was potassium instead of sodium was obtained. Hereinafter this compound is referred to as compound (29) K salt. The obtained compound (29) K salt showed purple in a flame test.

Maximum wavelength of absorbance ($H_2O$): 780 nm
Molar absorption coefficient ($H_2O$): 254,000
Maximum wavelength of fluorescence emission ($H_2O$): 800 nm Other aforementioned compounds are treated in the same manner as in this Example to give compounds having potassium counter ion instead of sodium.

These compounds having potassium counter ion are distinguished from the above compounds by attaching "K salt" after the corresponding compound numbers.

Example 12

In the same manner as in Example 11, compound (6) K salt was obtained. The obtained compound (6) K salt showed purple in a flame test.
Maximum wavelength of absorbance ($H_2O$): 788 nm
Molar absorption coefficient ($H_2O$): 226,000
Maximum wavelength of fluorescence emission ($H_2O$): 806 nm

Example 13

In the same manner as in Example 11, compound (2) K salt was obtained. The obtained compound (2) K salt showed purple in a flame test.
Maximum wavelength of absorbance ($H_2O$): 743 nm
Molar absorption coefficient ($H_2O$): 266,000
Maximum wavelength of fluorescence emission ($H_2O$): 762 nm

Example 14

In the same manner as in Example 11, compound (4) K salt was obtained. The obtained compound (4) K salt showed purple in a flame test.
Maximum wavelength of absorbance ($H_2O$): 753 nm
Molar absorption coefficient ($H_2O$): 212,000
Maximum wavelength of fluorescence emission ($H_2O$): 767 nm

Example 15

In the same manner as in Example 11, compound (3) K salt was obtained. The obtained compound (3) K salt showed purple in a flame test.
Maximum wavelength of absorbance ($H_2O$): 751 nm
Molar absorption coefficient ($H_2O$): 241,000
Maximum wavelength of fluorescence emission ($H_2O$): 767 nm

Example 16

The compound (6) K salt (50 mg) was dissolved in a small amount of water and passed through an ion exchange resin to convert potassium of the compound (6) K salt to proton. Thereto was added methanol saturated with sodium acetate to allow precipitation of crystals. This procedure was repeated twice. The resulting crystals were collected by filtration, washed with a small amount of methanol and dried to give (32 mg) of compound (6). The obtained compound (6) showed yellow in a flame test.

Figure 13:
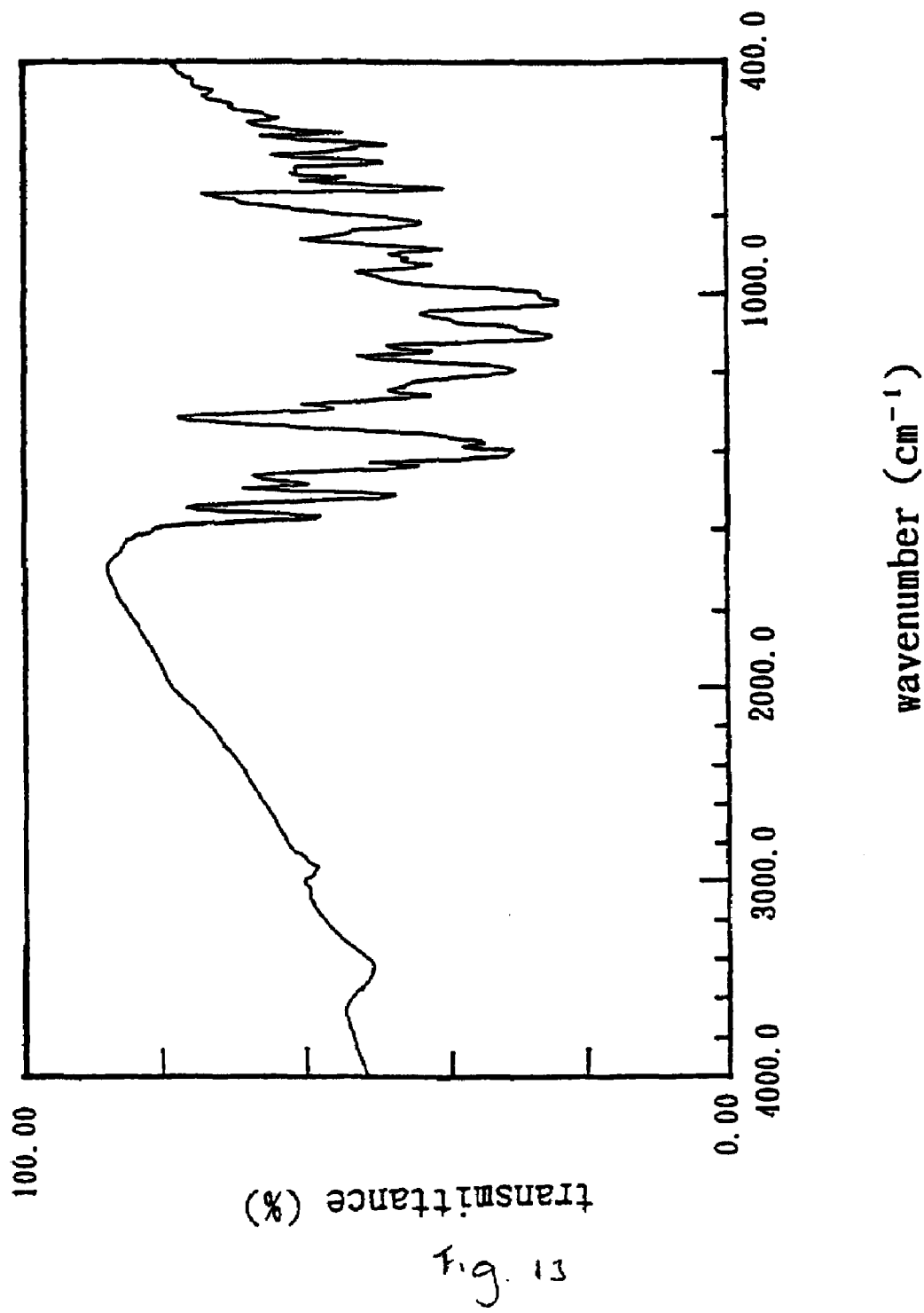
FIG. 13 is a chart showing the infrared absorption spectrum of compound (6).

The infrared absorption spectrum was measured for the obtained compound (6) by potassium bromide tablet method using a Fourier transform infrared spectrometer (VALOR-III, manufactured by JASCO). The following peaks were detected. The spectrum is shown in FIG. 13.
IR (vmax(KBr)): 1395, 1372, 1188, 1102, 1020 $cm^{-1}$

Example 17

Synthesis of Compound (54)

Figure 14:
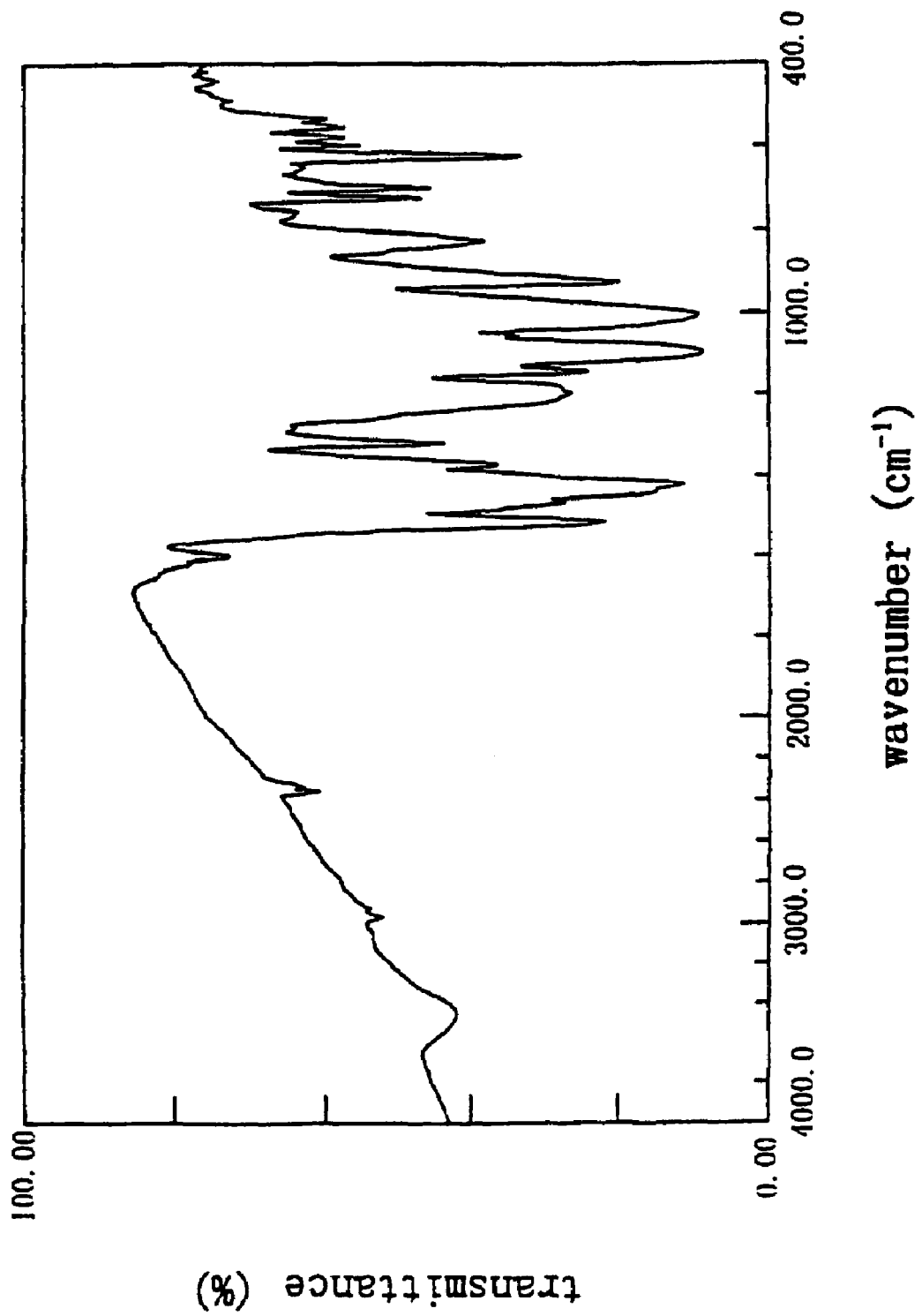
FIG. 14 is a chart showing the infrared absorption spectrum of compound (54).

To heterocyclic quaternary salt compound Q4 (3.5 g) were added methanol (20 ml), triethylamine (3.5 ml) and acetic anhydride (2 ml), and dianyl compound A1 (1.4 g) was added portionwise with stirring. The mixture was further stirred for 20 minutes. Acetic anhydride (1 ml) was added, and the mixture was stirred at room temperature for 1.5 hours. The insoluble matter was filtered off, and a solution of sodium acetate (4 g) in a small amount of methanol was added to the filtrate. The resulting crystals were collected by filtration and washed with a small amount of methanol. The crystals were dissolved in a small amount of water. Then the solution was diluted with methanol (10 ml), and the mixture was stirred at room temperature for 1 hour. The resulting crystals were collected by filtration, washed with a small amount of methanol and dried to give 1.5 g of compound (54). The obtained compound (54) showed yellow in a flame test.
Maximum wavelength of absorbance ($H_2O$): 743 nm
Molar absorption coefficient ($H_2O$): 244,000
Maximum wavelength of fluorescence emission ($H_2O$): 766 nm The infrared absorption spectrum was measured for the obtained compound (54) by potassium bromide tablet method using a Fourier transform infrared spectrometer (VALOR-III, manufactured by JASCO). The following peaks were detected. The spectrum is shown in FIG. 14.
IR (vmax(KBr)): 1511, 1421, 1099, 1004, 926 $cm^{-1}$

Experimental Example 1

The partition coefficient (log Po/w) of n-butanol/water was determined with respect to compound (29), compound (43), compound (45), compound (31), compound (3) K salt, compound (11) [available from Nippon Kankoh-Shikiso Kenkyusho CO., LTD. as NK-3261], compound (6) K salt, compound (2) K salt, compound (4) K salt, compound (34) and compound (54).

As a control compound, used were NK-1967 (Nippon Kankoh-Shikiso Kenkyusho CO., LTD.) and ICG (Tokyo Kasei Kogyo) having only 2 sulfonic acid groups in a molecule. The results are shown in Table 4.

TABLE 4

| Compound | Number of sulfonic acid group | log Po/w (butanol/water) |
|---|---|---|
| Compound (29) | 6 | −2.00 or less |
| Compound (43) | 5 | −2.00 or less |
| Compound (45) | 5 | −2.00 or less |
| Compound (31) | 4 | −2.00 or less |
| Compound (3) K salt | 4 | −2.00 or less |
| Compound (11) (NK-3261) | 4 | −2.00 or less |
| Compound (6) K salt | 4 | −2.00 or less |
| Compound (2) K salt | 4 | −2.00 or less |
| Compound (4) K salt | 4 | −1.51 |
| Compound (34) | 4 | −1.49 |
| Compound (54) | 4 | −2.00 or less |

TABLE 4-continued

| Compound | Number of sulfonic acid group | log Po/w (butanol/water) |
|---|---|---|
| NK-1967 | 2 | 0.34 |
| ICG | 2 | 1.41 |

Experimental Example 2

Fluorescence Imaging Test (1)

Tumor tissue pieces of mouse colon carcinoma (colon 26 carcinoma) were subcutaneously grafted to the left breast of BALB/c nude mice (5 weeks old, Clea Japan, Inc.). Ten days later when the tumor grew to a diameter of about 8 mm, the mice were subjected to the test.

As a fluorescence excitation light source, a titanium sapphire laser was used. The test mice were uniformly exposed to the laser light using a ring type light guide (Sumita Optical Glass Co.) wherein dispersion of irradiation was within 10%. The irradiation power output was adjusted so that it was about 40 μW/cm$^2$ near skin surface of the mice. The fluorescence was excited at the maximum excitation wavelength of each compound and fluorescence emission from the mice was detected and photographed through a short wavelength cutoff filter (IR84, IR86, IR88, Fuji Photo Film CO., LTD.) with a CCD camera (C4880, Hamamatsu Photonics K.K.). The cutoff filter was selected to fit the excitation wavelength of the compound. The exposure time was adjusted depending on the fluorescence intensity of each compound.

The test compounds used were compound (29), compound (31) and compound (6) K salt of the present invention, and NK-1967 and ICG having only 2 sulfonic acid groups in a molecule as control compounds. Each test compound (0.5 mg/ml) was dissolved in distilled water and administered to the mice via a tail vein. The dose was 5.0 mg/kg for compound (31), compound (6) K salt, NK-1967 and ICG, and 0.5 mg/kg for compound (29). At 24 hours after the administration of the compounds, the mice were anesthetized with diethyl ether and fluorescent light images of the entire body of the mice was photographed. The results are shown in FIGS. 1 to 5.

The compound (29) having a benzotricarbocyanine structure and six sulfonic acid groups, as well as compound (6) K salt and compound (31) both having a tricarbocyanine structure and four sulfonic acid groups obviously generated clearer images of tumor as compared to control compounds (NK-1967 having benzotricarbocyanine structure and ICG having tricarbocyanine structure) having two sulfonic acid groups. In particular, compound (29) could clearly depict the tumor even at a low dose and was noticeably effective.

Experimental Example 3

Fluorescence Imaging Test (2)

Nude mice were used for the test. compound (29) of the present invention and control compound ICG were intravenously injected from the tail vein at a dose of 5.0 mg/kg each under sevoflurane continuous inhalation anesthesia. At the same time, intermittent photographing of the fluorescence images was initiated. For photographing of the fluorescence images, exposure to excitation laser beam and extraction of fluorescence through a filter were done, wherein exposure time was one second. At 20 seconds after the administration of the compounds, blood vessel was suitably imaged. The fluorescence images were photographed until 5 minutes after the administration. FIGS. 6 to 9 show fluorescence images of the entire body of the mice at 20 seconds and 5 minutes after the administration.

ICG failed to contrastively show blood vessel in 5 minutes, whereas compound (29) could image the blood vessel for longer time than ICG.

Experimental Example 4

Residence in Blood Vessel

In the same manner as in Experimental Example 2, tumor tissue pieces were grafted to CDF, mice (female, 5 weeks old, Japan SLC, Inc.), and about 2 weeks later when the tumor grew to a diameter of about 1 cm, the mice were subjected to the test.

The test compounds were compound (29) K salt and compound (41) K salt having a benzotricarbocyanine structure and 6 sulfonic acid groups; compound (6) K salt, compound (4) K salt, compound (45) K salt, compound (31), compound (31) K salt, compound (3) K salt, compound (2) K salt, compound (43) K salt and compound (11) having a tricarbocyanine structure and 4-5 sulfonic acid groups; and control compounds ICG and NK-1967. Each test compound was dissolved in distilled water (0.5 mg/ml) and used. The obtained each compound solution was administered from the tail vein of the mice (5.0 mg/kg). Blood was taken from the mice at 0.5, 1, 4 and 24 hours after the administration of the compounds and centrifuged to give plasma.

Figure 10:
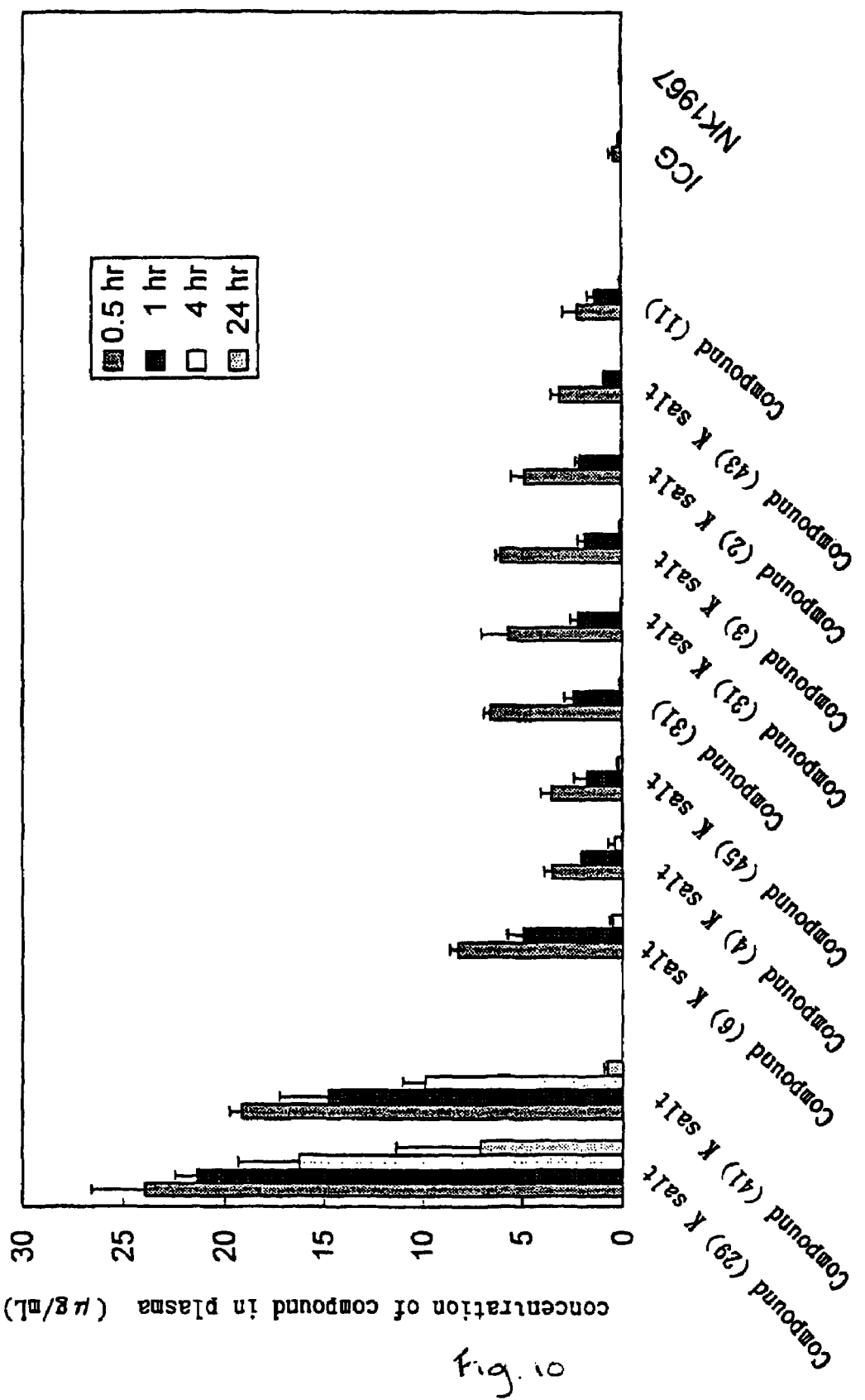
FIG. 10 is a graph showing the concentration of the compound in plasma at 0.5, 1, 4 and 24 hours after administration of the compound, wherein the axis of ordinates is concentration (µg/ml) of the compound in plasma at each time point.

The fluorescence intensity of the plasma was measured by a spectrofluorescence meter (RF 5300 PC, SHIMADZU CORPORATION). A calibration curve of each compound was drawn and compound concentration in plasma was calculated. The results are shown in FIG. 10.

The compounds of the present invention remained in plasma at high concentration for a long time.

Experimental Example 5

Acute Toxicity

Reduction of toxicity by the introduction of sulfonic acid group and reduction thereof by conversion into sodium salt were studied.

The test compounds were those listed in Table 5.

Each test compound was dissolved in distilled water to give a compound solution. This solution was intravenously injected to the conscious mice from the tail vein. The mice were monitored for 3 days after the administration, and acute toxicity [$LD_{50}$ (mg/kg body weight)] was estimated. The results are shown in Table 5.

TABLE 5

| Number of sulfonic acid group | Compound | $LD_{50}$ (mg/kg body weight) |
| --- | --- | --- |
| Three or more | compound (11)K salt | 350 |
| | compound (11) | 1980 |
| | compound (31)K salt | 350 |
| | compound (31) | >3550 |
| | compound (31)Ca salt | 2000 |
| | compound (31) pyridinium salt | 1000-2000 |
| | compound (45)K salt | 550 |
| | compound (45) | 1100-1220 |
| | compound (43)K salt | 300-350 |
| | compound (43) | 1630 |
| | compound (41)K salt | 470 |
| | compound (41) | >1010 |
| | compound (29)K salt | 470 |
| | compound (29) | >1010 |
| | compound (54) | >5000 |

TABLE 5-continued

| Number of sulfonic acid group | Compound | $LD_{50}$ (mg/kg body weight) |
| --- | --- | --- |
| | compound (6)K salt | 350 |
| | compound (3)K salt | 530 |
| | compound (4)K salt | 450 |
| | compound (2)K salt | 610 |
| Two or less | ICG | 70 |
| | NK1967 | 20 |

An increase in the number of sulfonic acid group in a molecule or conversion to a sodium salt resulted in striking reduction of acute toxicity.

The near infrared fluorescent contrast agent of the present invention is excited by an excitation light and emits near infrared fluorescence. This infrared fluorescence is superior in transmission through biological tissues. Thus, detection of lesions in the deep part of a living body has been made possible. In addition, the inventive contrast agent is superior in water solubility and low toxic, and therefore, it can be used safely.

What is claimed is:

1. A method of near infrared fluorescence imaging comprising introducing a pharmaceutical composition comprising a compound of the formula

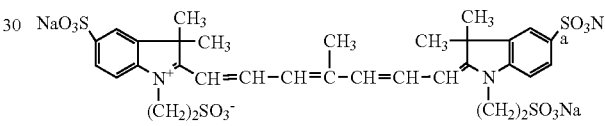

and a pharmaceutically acceptable carrier into a living body, exposing the body to excitation radiation, and detecting near infrared fluorescence from said compound.

2. A method of claim 1 for angiography.

3. A method of claim 1 for tumor imaging.

4. A method of claim 1 wherein said compound is administered in the form of a pharmaceutical composition with a pharmaceutically acceptable carrier which is an electrolyte, a buffer or a detergent.

* * * * *

UNITED STATES PATENT AND TRADEMARK OFFICE
CERTIFICATE OF CORRECTION

PATENT NO. : 7,547,721 B1  Page 1 of 1
APPLICATION NO. : 10/149917
DATED : June 16, 2009
INVENTOR(S) : Miwa et al.

It is certified that error appears in the above-identified patent and that said Letters Patent is hereby corrected as shown below:

Column 80, line 30 reads
"

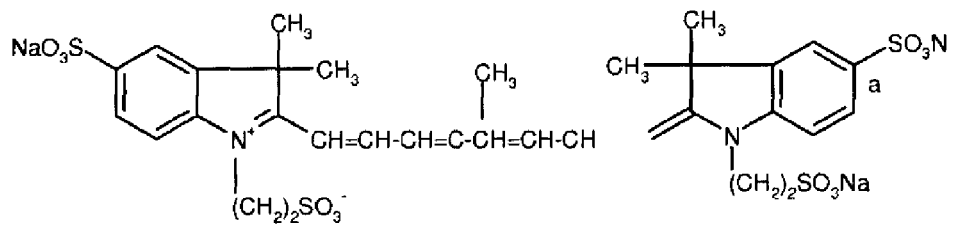

"

Should read
--

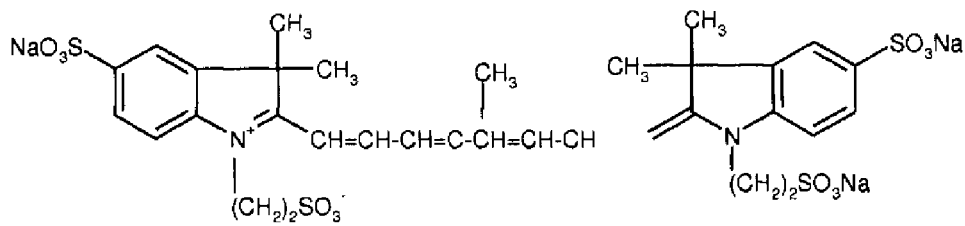

--

Signed and Sealed this

Twenty-fourth Day of November, 2009

David J. Kappos
*Director of the United States Patent and Trademark Office*